United States Patent
Salamone et al.

(10) Patent No.: US 11,590,259 B2
(45) Date of Patent: Feb. 28, 2023

(54) COMPOSITION AND KITS FOR PSEUDOPLASTIC MICROGEL MATRICES

(71) Applicant: ROCHAL INDUSTRIES, LLC, San Antonio, TX (US)

(72) Inventors: Joseph Charles Salamone, San Antonio, TX (US); Ann Beal Salamone, San Antonio, TX (US); Katelyn Elizabeth Reilly, San Antonio, TX (US); Laura Jean Suggs, Austin, TX (US); Eunna Chung, Seoul (KR); Kelly Xiaoyu-Chen Leung, San Antonio, TX (US)

(73) Assignee: ROCHAL TECHNOLOGIES LLC, Fort Worth, TX (US)

(*) Notice: Subject to any disclaimer, the term of this patent is extended or adjusted under 35 U.S.C. 154(b) by 0 days.

(21) Appl. No.: 17/348,468

(22) Filed: Jun. 15, 2021

(65) Prior Publication Data

US 2021/0308323 A1    Oct. 7, 2021

Related U.S. Application Data

(62) Division of application No. 14/689,625, filed on Apr. 17, 2015, now abandoned.

(51) Int. Cl.
| | |
|---|---|
| A61L 27/22 | (2006.01) |
| A61L 27/26 | (2006.01) |
| A61L 27/36 | (2006.01) |
| A61L 27/38 | (2006.01) |
| A61L 27/18 | (2006.01) |
| A61L 27/24 | (2006.01) |
| A61L 27/52 | (2006.01) |
| A61L 27/54 | (2006.01) |

(52) U.S. Cl.
CPC ............. *A61L 27/22* (2013.01); *A61L 27/18* (2013.01); *A61L 27/225* (2013.01); *A61L 27/227* (2013.01); *A61L 27/24* (2013.01); *A61L 27/26* (2013.01); *A61L 27/3604* (2013.01); *A61L 27/3633* (2013.01); *A61L 27/38* (2013.01); *A61L 27/3834* (2013.01); *A61L 27/52* (2013.01); *A61L 27/54* (2013.01); *A61L 2300/406* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 3,408,429 A | 10/1968 | Wichterle | |
| 4,172,066 A | 10/1979 | Zweigle | |
| 4,927,636 A * | 5/1990 | Hijiya | ............... A61K 9/205 424/78.18 |
| 5,733,563 A | 3/1998 | Fortier | |
| 6,129,761 A | 10/2000 | Hubbell | |
| 6,150,505 A | 11/2000 | Marx | |
| 6,290,729 B1 * | 9/2001 | Slepian | ............. A61M 25/1011 623/23.72 |
| 6,818,018 B1 * | 11/2004 | Sawhney | ............... A61L 27/34 523/113 |
| 7,442,397 B2 | 10/2008 | Zhang | |
| 7,582,311 B1 | 9/2009 | Cleland | |
| 7,651,703 B2 | 1/2010 | Cleland et al. | |
| 7,776,240 B2 | 8/2010 | Chu | |
| 8,038,721 B2 | 10/2011 | Love | |
| 8,323,794 B2 | 12/2012 | Chu | |
| 8,357,402 B2 | 1/2013 | Ingram | |
| 8,574,629 B2 | 11/2013 | Gavard Molliard | |
| 8,802,436 B1 | 8/2014 | Kentner | |
| 8,858,925 B2 | 10/2014 | Seliktar | |
| 2003/0045690 A1 | 3/2003 | Marx | |
| 2003/0166867 A1 | 9/2003 | Marx | |
| 2004/0208938 A1 | 10/2004 | Ramstack | |
| 2004/0220296 A1 | 11/2004 | Lowman | |
| 2005/0118144 A1 | 6/2005 | Zhang | |
| 2005/0281880 A1 | 12/2005 | Wang | |
| 2006/0233854 A1 | 10/2006 | Seliktar et al. | |
| 2008/0268056 A1 | 10/2008 | Joshi | |
| 2009/0053276 A1 | 2/2009 | Richard | |
| 2009/0202642 A1 | 8/2009 | Huang et al. | |

(Continued)

FOREIGN PATENT DOCUMENTS

| | | |
|---|---|---|
| JP | H0789867 | 4/1995 |
| WO | 94/01483 | 1/1994 |

(Continued)

OTHER PUBLICATIONS

Seetharaman, S. et al. 2011. A PEGylated fibrin-based wound dressing with antimicrobial and angiogenic activity. Acta Biomaterialia 7: 2787-2796; specif, pp. 2789, 2790, 2793, 2794.*

Bicerano, J. et al. 1999. Model for the viscosity of particle dispersions. Reviews in Macromolecular Chemistry and Physics C39(4): 561-642; specif, p. 563.*

Seetharaman, S. et al. 2011. A PEGylated fibrin-based wound dressing with antimicrobial and angiogenic activity. Acta Biomaterialia 7: 2787-2796; specif, pp. 2788, 2789, 2790, 2793.*

(Continued)

*Primary Examiner* — Renee Claytor
*Assistant Examiner* — Sharon M. Papciak
(74) *Attorney, Agent, or Firm* — Duane Morris LLP; Gregory M. Lefkowitz; Brandon A. Chan

(57) ABSTRACT

This invention relates generally to water-insoluble but water-swellable and deformable crosslinked PEGylated microgel particles of proteins and protein-based macromolecules that are pseudoplastic (shear thinning) and flow in aqueous media under shear and which can be injected or made to flow, wherein said microgel particles can reform as a cluster of microgel particles when shearing forces are removed. The microgel particles function as a matrix to support cell growth, viability, and proliferation.

17 Claims, 12 Drawing Sheets

(56) References Cited

U.S. PATENT DOCUMENTS

| | | | |
|---|---|---|---|
| 2010/0028435 A1 | 2/2010 | Molliard | |
| 2010/0137510 A1 | 6/2010 | Seliktar | |
| 2010/0226985 A1* | 9/2010 | Van Tomme | A61K 47/36 |
| | | | 424/486 |
| 2010/0330184 A1 | 12/2010 | Cleland | |
| 2011/0077737 A1 | 3/2011 | Stroumpoulis | |
| 2011/0238000 A1 | 9/2011 | Seliktar | |
| 2012/0034271 A1 | 2/2012 | Shu | |
| 2012/0070427 A1* | 3/2012 | Kaplan | A61K 47/42 |
| | | | 424/94.1 |
| 2012/0264190 A1* | 10/2012 | Christman | A61P 41/00 |
| | | | 435/219 |
| 2013/0189230 A1 | 7/2013 | Shoichet | |
| 2013/0209370 A1 | 8/2013 | Barry | |
| 2014/0170224 A1* | 6/2014 | Li | A61K 36/00 |
| | | | 424/492 |

FOREIGN PATENT DOCUMENTS

| | | | |
|---|---|---|---|
| WO | 95/26761 | 10/1995 | |
| WO | 2013/126799 | 8/2013 | |
| WO | WO-2013126799 A1 * | 8/2013 | A61F 9/00 |

OTHER PUBLICATIONS

Yan, C. et al. 2010. Rheological properties of peptide-based hydrogels for biomedical and other applications. Chemical Society Reviews 39: 3528-3540; specif, pp. 3528, 3529, 3531,3535.*

Guvendiren, M. et al. 2012. Shear-thinning hydrogels for biomedical applications. Soft Matter 8: 260-272; specif, pp. 269, 270.*

Boateng, J.S. 2008. Wound healing dressings and drug delivery systems: a review. Journal of Pharmaceutical Sciences 97(8): 2892-2923; specif, pp. 2892, 2893, 2899.*

Adams, S. et al. 2004. Influence of particle modulus on the rheological properties of agar microgel suspensions. Journal of Rheology 48(6): 1195-1213; specif, pp. 1195, 1198, 1200.*

Zhang, Ge, et al., "A PEGylated Fibrin Patch for Mesenchymal Stem Cell Delivery," Tissue Engineering, 2006, vol. 12, No. 1, pp. 9-19.

Prata, et al., "Complex fluids based on methacrylated hyaluronic acid," Biomacromolecules, 11(3),769-75, (abstract), [online], retrieved from PubMed, PMID: 20148576, Mar. 2010.

Ricci, et al., "Rheological characterization of Poloxamer 407 lidocaine hydrochloride gels," Eur J. Pharm Sci., 17(3): 161-7, (abstract), [online], retrieved from PubMed, PMID: 12393144, Nov. 2002.

Jones, et al. "An examination of the rheological and mucoadhesive properties of poly(acrylic acid) organogels designed as platforms for local drug delivery to the oral cavity," J. Pharm Sci. 96(10):2632-2646, (abstract), [online], retrieved from PubMed, PMID: 17702045, Oct. 2007.

"Rheology fundamentals of slurry"—relationship between particle size, particle shape and zeta potential, Web page of Malvern Panalytical, seminar material, [retrieved on Jan. 31, 2020], retrieved from the internet: <URL: materials-talks.jp/files/20180226142620_0.pdf>.

English translation of Notification of Reasons for Refusal received in corresponding Japanese patent application No. 2017-553385, dated Jan. 31, 2020.

Botchu V. S. Jyoti & Seung Wook Baek (2015) "Formulation and Comparative Study of Rheological Properties of Loaded and Unloaded Ethanol-Based Gel Propellants," Journal of Energetic Materials, 33:2, 125-139, DOI: 10.1080/07370652.2014.939311.

Guvendiren, M. et al. 2012. "Shear-thinning hydrogels for biomedical applications." Soft Matter 8: 260-272. specif. p. 269.

Pourjavadi, A. et al. 2008. "Salt- and pH-resisting collagen-based highly porous hydrogel." Polymer Journal 40(2): 94-103. specif, pp. 95, 102, 103.

Haque, M.A. et al. 2012. "Super tough double network hydrogels and their application as biomaterials." Polymer 53: 1805-1822, specif, pp. 1805, 1806, 1813, 1818.

Yan, C. et al. 2010. "Rheological properties of peptide-based hydrogels for biomedical and other applications." Chemical Society Reviews 39(9): 3528-3540; see NIH Public Access page numbering, pp. 1-28. specif, p. 1.

Jones, L.L. et al. 2002. "Spinal cord injury elicits expression of keratan sulfate proteoglycans by macrophages, reactive microglia, and oligodendrocyte progenitors." Journal of Neuroscience 22(11): 4611-4624. specif, p. 4611.

Annabi, N. et al. 2010. "Controlling the porosity and microarchitecture of hydrogels for tissue engineering." Tissue Engineering: Part B 16(4): 371-383. specif, pp. 371,372.

Wang, P. et al. 2009. "Viscoelastic properties of polyethylene glycol (PEG) boundary layers near a solid substrate." Journal of Physical Chemistry C 113: 729-735. specif, p. 734.

Nakama, T. et al. 2004. "Temperature- and pH-controlled hydrogelation of poly(ethylene glycol)-grafted hyaluronic acid by inclusion complexation with alpha-cyclodextrin." Polymer Journal 36(4): 338-344. specif, pp. 338, 342.

Cheng, G. et al. 2010. "Hydrogelation and self-assembly of Fmoc-tripeptides: unexpected influence of sequence on self-assembled fibril structure, and hydrogel modulus and anisotropy." Langmuir 26(7): 4990-4998. specif, pp. 4990, 4991, 4996, 4997.

Castellanos, M.M. et al. 2014. "Both protein adsorption and aggregation contribute to shear yielding and viscosity increase in protein solutions." Soft Matter 1 O: 122-131. specif, pp. 122, 123, 125.

Maltese, A. et al. 2006. "Novel polysaccharides-based viscoelastic formulations for ophthalmic surgery: rheological characterization." Biomaterials 27: 5134-5142. specif, pp. 5134, 5136, 5137.

Seetharaman, S. et al. 2011. "A PEGylated fibrin-based wound dressing with antimicrobial and angiogenic activity." Acta Biomaterialia 7: 2787-2796. specif, pp. 2787, 2788, 2789, 2795.

Yazdani-Pedram, M. et al. 2000. "Hydrogels based on modified chitosan, 1." Macromolecular Chemistry and Physics 201 (9): 923-930. specif, pp. 923, 924.

Boateng, J.S. et al. 2008. "Wound healing dressings and drug delivery systems: a review." Journal of Pharmaceutical Sciences 97(8): 2892-2923. specif, pp. 2892, 2893, 2899, 2902, 2904, 2905.

Van Vlierberghe, S. et al. 2011. "Biopolymer-based hydrogels a scaffolds fortissue engineering applications: a review," Biomacromolecules 12: 1387-1408. specif, pp. 1387, 1396.

Kirn, 1-Y et al. 2007. "Evaluation of semi-interpenetrating polymer networks composed of chitosan and poloxamer for artificial skin." Key Engineering Materials 342-343: 269-272. specif, pp. 269, 272.

* cited by examiner

COMPOSITION AND KITS FOR PSEUDOPLASTIC MICROGEL MATRICES

CROSS-REFERENCE TO RELATED APPLICATIONS

This application is a divisional of U.S. application Ser. No. 14/689,625, filed Apr. 17, 2015, the entirety of which is incorporated by reference herein.

FIELD OF THE INVENTION

This invention relates generally to crosslinked, water-swellable microgel particles of proteins and protein-based biological macromolecules that are pseudoplastic and flow in aqueous media under shear and which can be coated, injected, sprayed, painted, or implanted in tissues, organs, and wound void spaces as well as surround tissue substitutes, where the microgel particles aggregate as a monolithic microgel cluster in the absence of shearing forces. The microgel particles function as a viscoelastic matrix to support cell growth, viability, and proliferation.

BACKGROUND

The field of hydrogels for use as biologically-compatible macromolecules has been intensively investigated, commencing with their commercial use as monolithic, crosslinked, soft contact lens materials (U.S. Pat. No. 3,408,429). Because of their soft, flexible nature, hydrogels are excellent materials for many biomedical applications, including extended wear silicone-hydrogel contact lenses, delivery of drugs and other pharmaceutically active ingredients, development of new biomaterials, coating of biomaterials, bioadhesives and sealants for cell encapsulation and delivery, and cell culture substrates and scaffolds for tissue regeneration.

Both natural and synthetic polymers can be used to create scaffolds for tissue engineering applications. Natural polymers often have inherent biocompatibility and can be biologically active. Commonly used natural polymers that can be used as cell scaffolds include collagen, hyaluronan, fibrin, fibrinogen, silk, alginate, chitosan, dextran, and agarose, among others.

Synthetic polymer-based cell scaffolds allow control over physical and chemical properties, such as stability, degradation kinetics, physical properties, and mechanical strength. Many synthetic polymers have been investigated for use as a matrix for tissue engineering scaffolds, including poly(ethylene glycol) (PEG), poly(lactic acid), poly(glycolic acid), poly(lactic-co-glycolic acid), polycaprolactone, poly(hydroxyalkanoate)s, and poly(vinyl alcohol). In particular, PEG has been widely used as a scaffold material because of its unique chemical and physical properties, such as solubility in water and in organic solvents, nontoxicity, low protein adhesion and nonimmunogenicity. In addition, PEG includes hydroxyl end-groups that facilitate polymer modification, creating novel structures and architectures with different chemical, physical, and biological properties, particularly with biological moieties to enhance their biological activity. Poly(ethylene glycol) has often been used in combination with other polymers, to create scaffolds for the purpose of regenerating a number of tissues, including cartilage, bone, nerve, vasculature and muscle.

Compositions and methods for forming hydrogels in situ are discussed in U.S. Pat. No. 6,818,018 through a combination of physical and chemical crosslinking processes. The in situ formed hydrogels may be applied in conjunction with bioactive molecules that either are dissolved or dispersed within the hydrogels. Methods of using such hydrogels as tissue coatings to prevent postsurgical adhesion, as tissue augmentation or luminal occlusion aids, as matrices for carrying cells, drugs or other bioactive species, as tissue sealants or adhesives, and as medical device coatings also are presented.

In U.S. Pat. Nos. 7,776,240 and 8,323,794, injectable hydrogel microspheres are described by forming an emulsion where hydrogel precursors are in a dispersed aqueous phase and the hydrogel precursors are polymerized, yielding cross-linked microspheres. Preferably, the hydrogel precursors are poly(ethylene glycol) diacrylate and N-isopropylacrylamide and the continuous phase of the emulsion is an aqueous solution of dextran and a dextran solubility reducer. Proteins, such as cytokines, can be loaded into the microspheres.

U.S. Patent Application Publication Number 2004/0220296 discloses a gel formulation comprising poly(N-isopropylacrylamide), which is also injectable in a liquid form. Solutions of this polymer, copolymers or mixtures of the polymer with a second polymer such as poly(ethylene glycol), polyvinylpyrrolidone or poly(vinyl alcohol) are liquids at room temperature and solids at body temperature. Methods are described of implanting a hydrogel into a mammal by injecting the solution as a liquid at a temperature below body temperature, which then undergoes thermal phase transition to form a solid hydrogel in situ in the body as the implant warms to body temperature.

In U.S. Patent Application Publication Number 2008/0268056 a biocompatible substance is described that is useful for repairing a vertebral compression fracture. The biocompatible substance can be made from two or more biocompatible polymeric hydrogels via physical crosslinking. The biocompatible substance thus made is thermoresponsive and exhibits a lower critical solution temperature. It undergoes volume and stage changes with temperature in the range of 25° C.-34° C. The biocompatible substance can be in a liquid injectable form at room temperature and can gel within the human body at higher temperature. Other thermoresponsive hydrogels for injection based upon synthetic polymers are described in U.S. Patent Application Publication Number 2009/0053276.

Processes for the preparation of injectable hyaluronan hydrogels are reported in U.S. Patent Application Publication Number 2005/0281880. The processes include cross-linking one or more polymers and washing the subsequently formed gel, followed by purification and homogenization by impeller stirring to produce an injectable hydrogel. The swelling degree of the gels in phosphate buffered saline can be about 4,000-5,000%. The gels can have particle sizes on the order of 500 micrometers. The crosslinking reaction can be carried out with a bi- or polyfunctional crosslinking agent, such as an epoxide, aldehyde, polyaziridyl or divinyl sulfone. The crosslinking agent can be 1,4-butanediol diglycidyl ether. The process can be carried out at a pH of 11 or higher at a temperature of 37-60° C.

In U.S. Pat. No. 4,172,066, spheroidal microgels of a water-swellable or water-swollen, crosslinked polymer consisting essentially of water-soluble ethylenically unsaturated monomers are described that are dispersed in water or other aqueous media and are effective thickening agents which, when dispersed in an aqueous medium, exhibit pseudoplastic rheology. Because of their uniform small particle size, with water-swollen diameters generally within the range from about 0.5 to about 200 micrometers, and their ability to absorb substantial proportions of water, the microgels are particularly suited for applications requiring thickening agents, such as rapid sorption of aqueous fluids, e.g., sanitary articles such as diapers, belt pads and the like, and for applications wherein the swelling or partial plugging properties of the polymer are particularly important, e.g., in the plugging of porous formations or structures.

U.S. Pat. No. 8,038,721 discloses a soft, non-toxic tissue filler that consists of spherically shaped solid particles having a textured surface of a size range of between about 32 and 90 microns. The particles are suspended evenly in a gel as a carrier, where the solid particles are preferably a non-ceramic cured polymer such as poly(methyl methacrylate). The gel is a combination of a cellulose polysaccharide, such as carboxymethylcellulose, and an alcohol, such as poly(vinyl alcohol), dissolved in water or some other solvent. The filler is used by injection in order to augment a patient's soft tissue as well as to correct soft tissue defects.

An injectable gel is described in U.S. Pat. No. 8,574,629, comprising a cross-linked biopolymer-based matrix in which previously cross-linked biopolymer particles have been co-cross-linked with the matrix, where the biopolymer is selected from the group consisting of sodium hyaluronate, chondroitin sulfate, keratan, keratan sulfate, heparin, heparan sulfate, cellulose and its derivatives, alginates, xanthan, carrageenan, proteins, nucleic acids and mixtures thereof, and wherein the crosslinking agent is butanediol diglycidyl ether.

U.S. Patent Application Publication Number 2012/0034271 discloses an injectable in situ disulfide-bond cross-linked hydrogel, whose gelation process is completed in a syringe, wherein the thiol groups are oxidized into disulfide bonds to form the cross-linked hydrogel by oxygen dissolved in the crosslinking active solution in the sealed injectable container, where the in-situ crosslinked hydrogel is a derivative of polysaccharides, proteins or synthetic macromolecules produced by one or more chemical modifications.

A slowly polymerizing, biocompatible, biodegradable polymer capable of crosslinking to form a hydrogel that delivers isolated cells into a patient to create an organ equivalent or tissue, such as cartilage, is reported in U.S. Pat. No. 6,129,761. The polymer is selected from the group consisting of modified hyaluronic acids, synthetic modified alginates, polymers that are covalently crosslinkable by a radical reaction and polymers that gel by exposure to monovalent ions. The gels are reported to promote engraftment and provide three-dimensional templates for new cell growth. In one embodiment, cells are suspended in a polymer solution and injected directly into a site in a patient, where the polymer crosslinks to form a hydrogel matrix having cells dispersed therein. In another embodiment, cells are suspended in a polymer solution which is poured or injected into a mold having a desired anatomical shape, then crosslinked to form a hydrogel matrix having cells dispersed therein, which can be implanted into a patient.

A microporous injectable, soft elastic, fully resorbable fibrin-based composition for use as a soft tissue lumen and void filler is described in U.S. Patent Application Publication Number 2013/0209370. The composition combines a fibrinogen component, a thrombin component, a plasticizer, and calcium-containing particles having an average diameter between 0.01 μm and 200 μm. The preparation of an injectable soft tissue void filler composition is described by mixing the components together and/or homogenizing said components.

In U.S. Pat. No. 6,290,729, thixotropic and pseudoplastic polymers are described that exhibit shear thinning, whereby a polymer becomes more fluent under shear, and reverts to a high-viscosity or gelled form on cessation of shear. The '729 patent describes the formation of coatings that can be controlled by introducing crosslinking agents, gelling agents or crosslinking catalysts together with the fluent material, or thermoresponsive behavior in the polymer, and then altering the conditions such that crosslinking and/or gelling occurs in situ. A method for controlling tissue repair or in-growth is described that includes applying a polymeric material, at a site where tissue growth may occur, wherein the polymeric material is applied in a first fluent state and then converted in situ to a second non-fluent state.

Methods of preparing an extracellular matrix powder are described in U.S. Patent Application Publication Number 2012/0264190. In the '190 Publication, the compositions can be used for the formation of three-dimensional graft constructs for implantation, injection, or the powdered or particulate extracellular matrix material may be dispersed in a gel or ointment for topical use to induce the repair of damaged or diseased tissues in a host. The composition is a thermally responsive hydrogel that is in a liquid form at room temperature and in gel form at a temperature greater than room temperature or at normal body temperature.

In U.S. Pat. No. 8,802,436, improved methods of manufacturing bioactive gels from an extracellular matrix that retain sufficient bioactivity to assist in tissue repair are presented by particularizing the extracellular matrix to a particle size in the range of about 1 μm to about 1,000 μm, solubilizing the particularized powder in sodium hydroxide, neutralizing the solubilized extracellular matrix with hydrochloric acid, and, optionally, freezing or lyophilizing the frozen extracellular matrix, and, optionally, reconstituting the lyophilized gel in water or saline. The final consistency of all gels is foam-like.

Injection vehicles suitable for administering particulate suspensions are described in U.S. Pat. No. 7,582,311. Examples include polymer-based formulations, associated pharmaceutical formulations, articles of manufacture, and kits. The injection vehicles are reported to include a pseudoplastic composition that improves injectability. The injection vehicle comprises a flexible molecule, such as hyaluronic acid or a derivative thereof, dissolved in a physiological buffer, such as saline.

In U.S. Patent Application Publication Number 2004/0208938, injectable compositions having improved injectability and methods for the preparation of such injectable compositions are described. In the '938 Publication, dry microparticles with an aqueous injection vehicle form a suspension, and the suspension is then mixed with a viscosity enhancing agent to increase the viscosity of the fluid phase of the suspension to the desired level for improved injectability.

U.S. Patent Application Publication Number 2010/0330184 describes injection vehicles suitable for administering particulate suspensions, such as polymer-based formulations, as well as associated pharmaceutical formulations, articles of manufacture, and kits. The injection vehicles of the '184 Publication are reportedly superior to conventional injection vehicles in that they include a pseudoplastic flexible polymer composition, such as solutions of hyaluronic acid, hyaluronic acid derivatives, and combinations thereof, which improve injectability, facilitating delivery of the desired dose.

An injectable polymer composition for use as a cell delivery vehicle is discussed in U.S. Patent Application Publication Number 2013/0189230. The injectible polymer composition of the '230 Publication includes at least one thermal gelling polymer (methyl cellulose), at least one anionic gelling polymer (hyaluronan), and a water-based carrier, and is reported to be shear-thinning, thixotropic and resorbable.

In U.S. Pat. No. 8,357,402, a flowable wound matrix material is presented that is comprised of particles of a collagen matrix, preferably a collagen/glycosaminoglycan (GAG) matrix, that, when hydrated, reportedly can be effectively delivered to the wound site. Reportedly, the flowable wound matrix can be effectively delivered into wounds having varying depths and geometries and provides a structural framework that serves as a scaffold for cell ingrowth.

In U.S. Pat. No. 7,442,397, methods and materials related to fibrin-based biomatrices are presented, where stem cells or progenitor cells can be delivered to a diseased heart using a fibrin-based biomatrix to assist or restore heart function. The '397 patent reportedly provides a method for repairing damaged tissue in a mammal by introducing, on or into a tissue in need of repair, a fibrinogen solution having stem or progenitor cells under conditions such that a fibrin biomatrix including the cells forms at or near the site of introduction. In one embodiment, the fibrinogen solution is PEGylated. The conditions for forming the fibrin biomatrix can include introducing a solution having a fibrinogen-converting agent (e.g., a serine protease such as thrombin) to the fibrinogen solution.

U.S. Pat. No. 5,733,563 reports hydrophilic water-swellable gels consisting of a crosslinked mixture of a bifunctionalized poly(ethylene oxide), activated with a suitable activating agent, dissolved in an aqueous solution and an albumin-type protein. The resulting hydrogels are based on the crosslinking of a protein, namely albumin of various sources including, for example, bovine serum albumin, with a bifunctional poly(alkene oxide), preferentially poly(ethylene oxide), and most preferably poly(ethylene glycol), or a mixture of bifunctional poly(alkene oxide)s of various molecular masses. The mechanical properties of the hydrogels can be improved by adding unreactive poly(ethylene glycol) or other inert polymers of high molecular masses. The novel hydrogels can be used for making contact lenses, controlled drug release devices, immobilization matrices for enzymes or cells of therapeutic interest, wound dressings and artificial skin.

A hydrogel system comprising polymer-conjugated albumin molecules for controlled release delivery of therapeutic agents is described in U.S. Patent Application Publication Number 2011/0238000. The polymer is a functionalized synthetic polymer, preferably PEG-diacrylate. The polymer-conjugated albumin is preferably mono-PEGylated albumin. The hydrogel system may comprise a matrix to which the polymer-conjugated albumin molecules are linked via a second functional group of the polymer. The matrix may be formed from the same polymer of the polymer-albumin conjugate.

U.S. Patent Application Publication Number 2010/0137510 reportedly discloses a polymer-protein precursor molecule that comprises a thiolated protein and at least two synthetic polymers covalently attached to thiol groups of the thiolated protein, each of the at least two synthetic polymers having a functional group, the functional group being selected capable of crosslinking with a functional group of at least one other synthetic polymer being covalently attached to at least one other polymer-protein precursor molecule so as to form a scaffold. The functional group may be an acrylate or vinyl sulfone, which are crosslinked by photoinitiation. Soluble proteins of PEG-collagen, PEG-albumin, and PEG-fibrinogen could be combined and photocrosslinked to form hydrogel scaffolds.

U.S. Patent Application Publication Number 2003/0166867 discloses fibrin nanoparticles having a mean diameter of 200-2000 nm (0.2-2.0 μm), and may be obtained by mixing an aqueous solution comprising fibrinogen, thrombin and Factor XIII in an oil emulsion at a temperature of 50-80° C., without the addition of an exogenous chemical cross-linking agent. Related U.S. Pat. No. 6,150,505 reports the preparation of fibrin microbeads of 50-200 μm in diameter by reacting fibrinogen and thrombin, in heated vegetable oil (70-80° C.), in the presence of endogenous factor XIII U.S. Pat. No. 8,858,925 reportedly discloses biodegradable scaffolds composed of a naturally-occurring protein backbone of fibrinogen crosslinked by a modification of the synthetic polymer poly(ethylene glycol) that generates a PEGylated-fibrinogen scaffold for use in treating disorders requiring tissue regeneration. The '925 patent uses a precursor molecule comprising a fibrinogen protein that is denatured and retains an activity of forming a scaffold and at least two poly(ethylene glycol) molecules covalently connected to free thiol groups of the denatured fibrinogen protein, where each of the at least two PEG molecules comprises a functional group for crosslinking in order to form hydrogel scaffolds. Crosslinking is performed by subjecting the precursor molecules to a free-radical polymerization reaction, preferably by photoinitiation of acrylated PEG's, which is done ex vivo or in vivo.

SUMMARY

Figure 1:
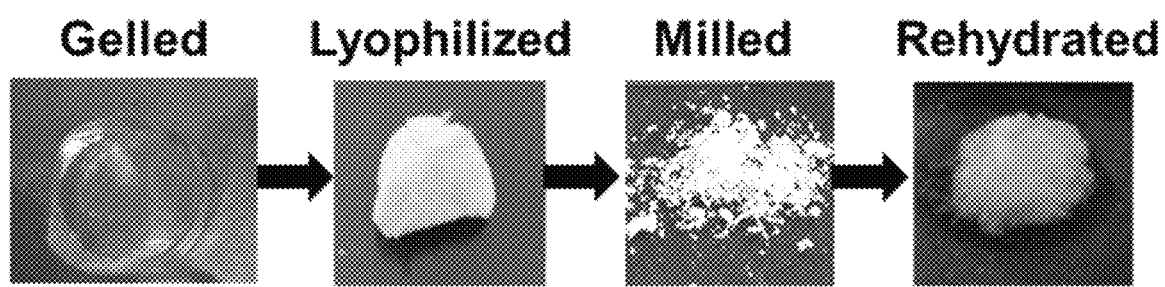
FIG. 1 shows images of the process for the preparation of PEGylated fibrin or PEGylated fibrinogen microgel powders.

Water-insoluble but water-swellable and deformable crosslinked PEGylated microgel particles of proteins, protein-based macromolecules, or both are described. The proteins and protein-based macromolecules can be selected from extracellular matrices, glycoproteins, structural proteins, fibrous proteins, enzymes, proteoglycans, natural polypeptides, synthetic polypeptides, globular proteins, membrane proteins, plasma proteins, peptides, oligopeptides, antimicrobial peptides, peptide hormones, chaperones, metalloproteins, hemoproteins, coagulation proteins, immune system proteins, ion channel proteins, cell adhesion proteins, neuropeptides, nucleoproteins, scleroproteins, chromoproteins, conjugated proteins, protein-protein complexes, protein-polysaccharide complexes, protein-lipid complexes, protein-enzyme complexes, protein-polymer complexes, motor proteins, mucoproteins, phosphoproteins, contractile proteins, transport proteins, signaling proteins, regulatory proteins, growth factors proteins, sensory proteins, defense proteins, storage proteins, receptor proteins, antibodies, recombinant proteins, fibrinogen, fibrin, thrombin, collagen, elastin, albumin, gelatin, keratin, laminin, and combinations thereof, which are pseudoplastic and flow in aqueous media under shear and which can be injected or made to flow, wherein the microgel particles can reform as a cluster of microgel particles when shearing forces are removed.

The crosslinked PEGylated microgel particles can also be utilized in their dried state and can be placed into or on a body defect, wound, burn, or in, on, or surrounding a tissue substitute, wherein the microgel particles can be hydrated by endogenous or exogenous sources.

Of particular interest is the use of such protein-based microgel particles as coated, injected, or implanted materials in tissues, organs, wound void spaces, tissue substitutes, and skin replacement products, where the hydrated microgel particles under shear in aqueous media are pseudoplastic and can reform to a cohesive microgel cluster when shear is removed. The microgel particles can be applied in either their dried state as a powder or as hydrated particles. The materials described herein can be utilized in methods that include filling biological voids, fissures, and soft tissue lumens, and providing a coating and support for skin substitutes, where the microgel particles function as a cell matrix.

Examples of voids include, but are not limited to, lesions, fissures, fistulas and diverticula. These voids can be physiological or the result of infection, surgery, cyst, tumor removal, or traumatic injury or remodeling of soft tissue, such as in skin and wound healing, plastic surgery, cosmetic surgery, reconstructive surgery, coating/sealing of skin replacement products, tendon repair, hernia repair, craniofacial surgery, ophthalmic surgery, cervicofacial rhytidectomy, abdominoplasty, breast augmentation, myocardium repair, cartilage repair, nerve repair, spinal cord repair, liver tissue regeneration, bladder repair, muscle repair, mastopexy, rheumatology, gynecomastia reduction, body contouring, skin rejuvenation, skin resurfacing, microsurgery, dermato-cosmetics for filling in wrinkles, masking scars or enhancing lips, and the like.

Skin replacement utilizing tissue engineered skin substitutes and spray-on cells is used to provide skin repair for difficult-to-heal wounds, such as chronic wounds due to diabetes, third-degree burns, and trauma wounds. Non-incorporation of the skin replacement product and wound infection can be key determinants for lack of success in wound healing using skin replacement products. Skin replacement products often fill approximately 60% of the wound void, leaving 40% of the wound area without continuous contact for cell mobility as well as open areas for desiccation/maceration and infection development. The microgel particle-containing formulations described herein form a coating that is conformable to surrounding tissues, filling wound void space when applied as a powder and hydrated in situ or applied as hydrated microgel particles, said hydrated microgel particles enhance cell mobility between skin replacement products and the wound bed, decreasing desiccation and maceration. When an antimicrobial agent is added to the microgel particles, infection can be reduced or eliminated, thereby improving healing effectiveness, particularly for tunneling and undermining wounds, burns, and skin replacement products that produce a higher take rate in clinical outcome.

The microgel particles are derived from naturally-occurring or genetically obtained proteins and protein-based biological macromolecules selected from collagen, extracellular matrix, albumin, plasma, fibrinogen, fibrin, thrombin, coagulation factors, Von Willebrand Factor, hemoglobin, elastin, gelatin, keratin, acellular dermis, amniotic membrane, adipose tissue, Matrigel, cadaveric fascia, heart valves, blood vessels, skin, nerves, skeletal muscle, mucin, aggrecan, actin, vitronectin, elastin, perlecan, keratin, spectrin, placenta, liver, pancreas, fibronectin, elastin, laminin, reticulin, chorion, umbilical cord, small intestinal submucosa, large intestine, bladder acellular matrix, stomach submucosa tissue, prostate, decorin, biglycan, perlecan, lumican, fibromodulin, integrins, cadherins, agrin, entactin, epiphycan, actin, pericardium, placenta, fetal tissue from any mammalian organ, virus derivatives, combinations thereof, and the like.

An injectable particle-based hydrated microgel is advantageous in filling soft tissue defects. The microgel particle-containing compositions can flow through an injection needle by deformation of the microgel, if required by the inner dimensions of the injection needle, and are shear thinning to allow filling of tunneling and undermining wounds because the discrete microgel particles can separate from a cluster of particles at rest under a movable force thus lowering the viscosity, and because the cluster of particles can reform when shear is removed, regenerating the pseudoplastic matrix by the formation of a moldable, conformable viscoelastic solid. The flowable characteristics of the hydrated microgel particles, in conjunction with their resulting viscoelastic solid-like behavior, enables the injectable, pseudoplastic matrix to fill irregular wound surfaces or fill tissue defects.

Preparation of derivatized proteins by PEGylation includes conversion of the protein component to a more hydrophilic state that is swellable but insoluble in aqueous media. The derivatized protein functions as a hydrogel; however, crosslinking of the derivatized proteins by multifunctional PEGylation can result in monolithic gelation in aqueous media. The monolithic gel can then be lyophilized and ground to a powder, which, upon hydration, forms microgel particles. PEGylation of proteins and protein-based macromolecules can occur through reaction with available amino or sulfhydryl groups, which are predominantly on the protein component. PEGylating agents often comprise reactive functional groups, including azide, carbonate, ester, aldehyde, acrylate, carboxyl, carbodiimide, carbonylimidazole, dichlorotriazine, epoxy, isocyanate, isothiocyanate, maleimide, nitrophenyl carbonate, orthopyridyl disulfide, pyridinyloxycarbonyl, succinimidyl carbonate, succinimidyl glutarate, succinimidyl methyl butanoate, succinimidyl succinate, succinic acid, sulfhydryl, tresylate, vinyl sulfone, and the like. Depending on the type of PEGylation agent used for derivatizing the proteins and/or protein-based macromolecules, other available functional groups, such as carboxyl, guanidino, hydroxyl, imidazole, or tyrosine (phenolic) groups can also be PEGylated. The molecular weight of the PEG component and its molar ratio to the protein or protein-based macromolecule to be PEGylated determines the degree of hydration to be obtained, the degree of crosslinking, as well as the resulting physical, mechanical, and biological properties of the PEGylated composite. In general, the larger the PEG segment, the higher the hydration (swelling) of the resulting gel, the stronger the gel, the greater the stability of the protein component of the gel from protease degradation, and the lower the biological activity of the composite. The reduced biological activity of the protein component of the composite may be related to steric hindrance caused by the poly(ethylene glycol) units and by overall dilution in the composition.

The mechanical properties of the microgels can be studied by rheometric analysis. In rheometry, the storage modulus (G') and loss modulus (G") of weak biological materials, such as ocular tissues (e.g., vitreous) and fat, are substantially lower than related values for strong materials, such as muscle, tendon, and cartilage. In this regard, values of G' range from 1 Pa to 1 MPa and values of G" range from 0.1 Pa to 1 MPa. In some embodiments described herein, the storage modulus ranges from 10 Pa to 250,000 Pa, or from 50 Pa to 175,000 Pa, or from 100 Pa to 100,000 Pa. In some embodiments, the loss modulus ranges from 5 Pa to 100,000 Pa, or from 7.5 Pa to 50 Pa, or from 10 Pa to 10,000 Pa.

In some embodiments, the crosslinked, hydrated, PEGylated microgel particles display pseudoplasticity under shear. This pseudoplastic phenomenon is based on the water-insoluble, hydrated particles themselves and not on soluble macromolecules. Additionally, the rheological behavior of the hydrated microgel particles described herein are surprisingly related to their solid-like behavior, as demonstrated by loss tangent (tan delta) values (G"/G') less than 1, as opposed to being more fluid-like.

In some embodiments, the disclosure provides crosslinked, water-swellable microgel particles of derivatized protein-based biological macromolecules.

In some embodiments, the disclosure provides protein-based biological macromolecules that are crosslinked by difunctional to multifunctional PEGylation.

In some embodiments, the disclosure provides that the molar ratio of PEGylating agent to protein ranges from 1:1 to 100:1.

In some embodiments, the disclosure provides for hydrated microgel particles that are pseudoplastic under shear in aqueous media.

In some embodiments, the disclosure provides for compositions where, when shear is removed from the hydrated microgel particles, a cluster of microgel particles reforms.

In some embodiments, the disclosure provides a dry microgel powder and hydrated microgel particles.

In some embodiments, the disclosure provides for microgel particles that can be coated, injected, sprayed, painted, or implanted in or on tissues, organs, wound void spaces, tissue substitutes, bandages, and medical devices.

In some embodiments, the disclosure provides methods to treat wounds that have tunneling and undermining with the microgel particles.

In some embodiments, the disclosure provides microgel particles that are water-insoluble but water-swellable and deformable under shear or compression.

In some embodiments, the protein portion of the microgel particles is selected from extracellular matrices, glycoproteins, structural proteins, fibrous proteins, enzymes, proteoglycans, natural polypeptides, synthetic polypeptides, globular proteins, membrane proteins, plasma proteins, peptides, oligopeptides, antimicrobial peptides, peptide hormones, chaperones, metalloproteins, hemoproteins, coagulation proteins, immune system proteins, ion channel proteins, cell adhesion proteins, neuropeptides, nucleoproteins, scleroproteins, chromoproteins, conjugated proteins, protein-protein complexes, protein-polysaccharide complexes, protein-lipid complexes, protein-polymer complexes, motor proteins, mucoproteins, phosphoproteins, contractile proteins, transport proteins, signaling proteins, regulatory proteins, growth factors proteins, sensory proteins, defense proteins, storage proteins, receptor proteins, antibodies, recombinant proteins, fibrinogen, fibrin, thrombin, collagen, elastin, albumin, gelatin, keratin, laminin, and combinations thereof.

In some embodiments, the protein portion of the microgel particles is selected from fibrinogen, fibrin, albumin, plasma, extracellular matrix and collagen.

In some embodiments, the microgel particles induce angiogenesis in vivo.

In some embodiments, the microgel particles promote transplanted cell survival in vivo.

In some embodiments, the protein PEGylating agent is multifunctional.

In some embodiments, the protein PEGylating agent is α-succinimidyloxyglutaryl-ω-succinimidyloxyglutaryloxy-polyoxyethylene (SG-PEG-SG).

In some embodiments, biologically active agents are incorporated into the PEGylated protein microgel.

In some embodiments, the biologically active agents are cells.

In some embodiments, the cells are of human origin and are either autologous or allogeneic.

In some embodiments, the cells are stem cells of human origin and are either autologous or allogeneic.

In some embodiments, it is a further object of the invention that the biologically active agent is micronized decellularized skin tissue.

In some embodiments, the biologically active agent is micronized or morselized tissue, such as, but not limited to, spinal cord, bladder, small intestinal submucosa, skin, dermis, epidermis, fat, cartilage, placenta, extracellular matrix, tendon, umbilical cord, cornea, heart, myocardium, liver, pancreas, and muscle.

In some embodiments, the biologically active agent is morselized amniotic tissue.

In some embodiments, the biologically active agent is minced tissue.

In some embodiments, the biologically active agent is micronized tissue.

In some embodiments, the biologically active agent is granulated crosslinked bovine tendon collagen and/or glycosaminoglycan.

In some embodiments, the biologically active agent is amniotic fluid.

In some embodiments, the biologically active agent is Wharton's jelly.

In some embodiments, the biologically active agent is micronized skin tissue.

In some embodiments, the biologically active agent is a growth factor.

In some embodiments, the biologically active agent has antimicrobial properties.

In some embodiments, the antimicrobial agent is poly(hexamethylene biguanide) and its salts.

In some embodiments, water-soluble polymers are added to the PEGylated microgel particles.

In some embodiments, essential oils are added to the PEGylated microgel particles.

In some embodiments, the crosslinked PEGylated microgel particles can be applied as a powder, liquid, gel, paste, cream, emulsion, or combinations thereof, In some embodiments, the rheological storage modulus (G') is greater than the loss modulus (G") for the hydrated microgel particles, with a loss tangent less than unity.

DETAILED DESCRIPTION

Compositions that include water-insoluble, microgel particles selected from crosslinked, PEGylated proteins and protein-based biological macromolecules that are pseudoplastic in aqueous solution are provided. The solution of hydrated microgel particles decreases in viscosity with applied shear and reforms into a microgel cluster in the absence of shear. The molar ratio of PEGylating agent to protein and protein-based biological macromolecules is from 1:1 to 100:1. In some embodiments, the concentration of microgel particles in the composition is from 10 mg/mL to 1,000 mg/mL, or from 25 mg/mL to 800 mg/mL, or from 50 mg/mL to 750 mg/mL, or from 100 mg/mL to 500 mg/mL. The individual and clustered hydrated microgel particles either alone or in a mixture can have viscoelastic solid properties, storage modulus greater than loss modulus, and loss tangent values less than 1.

Utilization of conventional monofunctional PEGylation for the preparation of water-insoluble, water-swellable PEGylated proteins is not generally preferred because soluble gels are often obtained, which do not provide the desired mechanical properties. Such soluble gels may provide a poor scaffold for added cells. In some embodiments for the preparation of water-insoluble, water-swellable PEGylated protein monolithic hydrogels described herein, PEGylation by multifunctional reactive groups, on the termini of a linear or branched, multi-armed poly(ethylene glycol) (PEG) is used to produce a monolithic gel in aqueous media that can be converted to insoluble microgel particles after drying and converting to particles, such as by milling, e.g., mortar and pestle or cryomilling. In some embodiments, microgel particles can be obtained directly during protein PEGylation preparation by rapid stirring or shearing of the resulting gel. In some embodiments, isolation of the monolithic gel is preferred because unreacted components can be separated by extraction prior to microgel particle formation.

In some embodiments, the PEGylation agents are selected from α-aminopropyl-ω-aminopropoxypolyoxyethylene, α-aminopropyl-ω-carboxypentyloxypolyoxyethylene, α,ω-bis{2-[(3-carboxy-1-oxopropyl)amino]ethyl}polyethylene glycol, α-[3-(3-maleimido-1-oxopropyl)amino]propyl-ω-[3-(3-maleimido-1-oxopropyl)amino]propoxypolyoxyethylene, pentaerythritol tetra(aminopropyl)polyoxyethylene, α-[3-(3-maleimido-1-oxopropyl)amino]propyl-ω-(succinimidyloxycarboxy)polyoxyethylene, pentaerythritol tetra(succinimidyloxyglutaryl)polyoxyethylene, pentaerythritol tetra(mercaptoethyl)polyoxyethylene, hexaglycerol octa(succinimidyloxyglutaryl)polyoxyethylene, hexaglycerol octa(4-nitrophenoxycarbonyl)polyoxyethylene, 4-arm poly(ethylene glycol) tetraacrylate, 4-arm succinimidyloxyglutaryl)polyoxyethylene, bis(polyoxyethylene bis[imidazoyl carbonyl]), O-(3-carboxypropyl)-O'-[2-(3-mercaptopropionylamino)ethyl]polyethylene glycol, O,O'-bis[2-(N-succinimidylsuccinylamino)ethyl]polyethylene glycol, O,O'-bis(2-azidoethyl)polyethylene glycol, poly(ethylene glycol) diacrylate, poly(ethylene glycol) diglycidyl ether, poly(ethylene glycol) di(p-nitrophenyl carbonate), poly(ethylene glycol) di(vinyl sulfone), poly(ethylene glycol) di(proprionaldehyde), poly(ethylene glycol) di(benzotriazolyl carbonate), and the like, and combinations thereof. In some embodiments, the PEGylation agent is α-succinimidyloxyglutaryl-ω-succinimidyloxyglutaryloxypolyoxyethylene (SG-PEG-SG), available from NOF America Corporation under the mark SUNBRIGHT® DE-034GS, with a molecular weight of 3,400 Daltons (CAS Number: [154467-38-6]). SG-PEG-SG is believed to crosslink proteins via elimination of N-hydroxysuccinimide of protein amino groups, forming carbamate bridges between multiple protein segments and the PEGylating agents. Thus, it is believed that the PEGylating agent forms a bridge between fibrinogen moieties.

In some embodiments, PEGylated fibrinogen and PEGylated fibrin hydrated microgel particles provide a convenient delivery format for utilization as a soft tissue filler, coating, implantation, or injection in or on tissues, organs, and wound void spaces as well as a conformable coating for tissue substitutes, serving as degradable scaffolds to manage the wound environment and promote angiogenesis during healing. Angiogenesis and neovascularization are critical determinants of wound healing outcomes as newly formed blood vessels participate in the healing process, providing oxygen and nutrients to cells and growing tissues. It is known that wound healing is facilitated by fibrinopeptides, the degradation products of fibrinogen and fibrin, which have a known role in enhancing angiogenesis and tissue regrowth.

In contrast to a monolithic hydrogel, the individual hydrated microgel particles have large pore sizes and large surface areas for cell attachment. In addition to the unique flow properties described herein, the flexibility and openness of the microgel particle system enables cell mobility. In some embodiments of the dried microgel particles, pore sizes range from 0.9 μm to 40.7 μm, while the length of the particles range from 10.9 μm to 1,347.7 μm and a width of 2.2 μm to 874.2 μm. In some embodiments of the dried microgel particles, pore sizes range from 0.9 μm to 23.7 μm, while the length of the particles range from 5.3 μm to 1,832.8 μm and a width of 1.6 μm to 894.2 μm. In some embodiments, the dried microgel particles are prepared by cryomilling or by mortar and pestle.

In some embodiments, when used as a cell scaffold, the dried microgel is rapidly rehydrated by a solution containing cells. In some embodiments, dry microgel powder is preloaded in a syringe, and cells are drawn into the syringe in order to hydrate the microgel powder before the cell-laden composition is injected into a wound or defect. In other embodiments, dry microgel powder is preloaded in a vial, then cells in solution are injected through the septum into the vial in order to hydrate the microgels, before the cell-laden system is drawn into a syringe and injected into tissue, a void, or a wound in need thereof. In some embodiments, the hydrated pseudoplastic cell composition can be injected through a syringe or cannula into tissue, a void, or a wound or applied by coating for localized delivery. Upon application, the hydrated microgel particles aggregate to form a microgel cluster by adhering to each other and to the surrounding tissue. The microgel cluster forms a cohesive hydrogel network that contains void spaces in and on the microgel particles as well as between the microgel particles. The shear thinning and rapid self-aggregating characteristics of the microgel particles, in conjunction with their ability to accommodate cells and other biological agents in void spaces, coupled with their ability to fill the shape of the cavity with an interface between the microgel and tissue, provides a superior network for delivery of biological agents. As a result, the water-insoluble, microgel particle compositions described herein provide an excellent system for cell delivery.

PEGylated fibrinogen particles that have been lyophilized and milled into a powder exhibit shear thinning, flowable behavior when rehydrated. In some embodiments, the microgel particles adsorb approximately 15 times their weight in saline solutions (93 wt % saline), and are more hydrated than analogous PEGylated fibrin particles, which adsorb approximately 7 times their weight in saline solution (89 wt % saline) at the same degree of PEGylation (mole ratio of 50:1, Table 1). Rather than forming a single solid gel, these PEG-fibrinogen microgel particles interact with adjacent PEG-fibrinogen microgel particles via hydrogen bonding to form a "gel-like" solid with shear thinning properties.

Among the advantages of the microgel particles described herein relative to a monolithic hydrogel prepared in situ in a host are that the injected product can be pre-purified to eliminate unreacted components; can be injected in hydrated microgel form to a designated location based on the shear thinning properties, which facilitates filling of soft tissue defects; can be stored at room temperature in powder form; and can be mixed with cells during a clinical procedure by drawing the cell solution into the syringe with the microgel powder or otherwise contacting the cell solution with the microgel powder. The porous network of the hydrated microgel particles also enables cell mobility and improves cell survival by nutrient exchange and host cell infiltration through its pores and void spaces. This flexibility is in direct contrast to a monolithic hydrogel, such as has been reported for poly(ethylene glycol) (PEG) hydrogels as scaffolds, which can be difficult for cells to infiltrate, due to the PEG hydrogel density (U.S. Pat. No. 8,557,288).

In addition, in situ preparation of a monolithic gel often utilizes photopolymerization of pendant acrylate groups on PEGylated materials, or other vinyl-type monomers. While such a procedure is cumbersome in a clinical environment, initiation of a free radical polymerization in situ also generates heat, which can be detrimental to surrounding tissue, or to added cells. Such a process also presents the possibility of residual, unreacted monomer remaining in the body, which may have cytotoxic behavior.

In some embodiments, the microgel particles described herein can be irregular in shape, or can have a defined shape, such as a sphere or ellipse. In some embodiments, the microgel particles can be microporous, mesoporous, or macroporous. Depending on the embodiment, the microgel particles can therefore have an adjustable size, an adjustable degree of hydration, a large surface area for cell attachment or addition of a biological agent, and an interior porous network for incorporation of other biomolecules. In addition, the microgel particles are inherently biodegradable. Furthermore, in contrast to a monolithic (bulk) hydrogel, because of their smaller size, flexibility, deformation and compression occur readily, the microgel particles are responsive to environmental changes.

In some embodiments, the pseudoplastic microgel particle compositions can include an aqueous solution with amniotic fluid, morselized amniotic tissue, minced tissue, micronized tissue, micronized decellularized tissue, plasma, blood, granulated cross-linked bovine tendon collagen and glycosaminoglycans, cells and stem cells in cell culture medium, synthetic or naturally derived extracellular matrix components, including collagen, glycosaminoglycans, fibrin, laminin, and fibronectin, hydroxyapatite, honey, polysaccharides, biodegradable polymers, including polyglycolides, polylactides, poly(lactide-co-glycolide), polydioxanone, polycaprolactone, poly(trimethylene carbonate), poly(propylene fumarate), polyurethanes, poly(ester amide)s, poly(ortho ester)s, polyanhydrides, poly(amino acid)s, polyphosphazenes, and bacterial polyesters, and combinations thereof, and which can be injected into soft tissue, a void or a wound.

In some embodiments, minced tissue is selected from skin tissue, muscle tissue, vascular tissue, nerve tissue, fat tissue, cartilage tissue, bone tissue, tendon tissue, bladder tissue, intestinal tissue, heart tissue, lung tissue, kidney tissue, liver tissue, pancreatic tissue, and vocal fold tissue. In some embodiments, micronized tissues and micronized decellularized tissues are selected from skin tissue, muscle tissue, vascular tissue, nerve tissue, fat tissue, cartilage tissue, bone tissue, tendon tissue, bladder tissue, intestinal tissue, heart tissue, lung tissue, kidney tissue, liver tissue, pancreatic tissue, and vocal fold tissue. The pseudoplastic microgel matrix can be used, for example, for the treatment of diabetic foot ulcers with tunneling and undermining, or in other wounds or surgical procedures where a flowable viscoelastic matrix is desirable.

Fibrinogen is a water-soluble glycoprotein in vertebrates that helps in the formation of blood clots. The fibrinogen molecule is a water soluble, 340 kDa plasma glycoprotein that is converted by thrombin into water-insoluble fibrin during blood clot formation. Fibrinogen has a rod-like shape with dimensions of approximately 9×47.5×6 nm with a negative net charge at physiological pH (isoelectric point of pH 5.2). Fibrinogen is available commercially from human plasma, bovine plasma, salmon plasma, baboon plasma, murine plasma, mouse plasma, rat plasma, canine plasma, and cat plasma. In some embodiments, human plasma is preferred. In some embodiments Sigma-Aldrich (F3879)

fibrinogen from human plasma is utilized containing 50-70% protein, wherein ≥80% of the protein is clottable. In some other embodiments, fibrinogen may be utilized from autologous, allogeneic, or xenogeneic sources. In still other embodiments, recombinant fibrinogen may be utilized. In some embodiments, autologous human fibrinogen is preferred.

Thrombin is a proteolytic enzyme that acts as a serine protease in converting fibrinogen into insoluble strands of fibrin, as well as, catalyzing many other coagulation-related reactions. Thrombin is available from several types of plasma, such as human, bovine, porcine, equine, rat, rabbit, and recombinant sources. In some embodiments Sigma Aldrich (T7009) thrombin from human plasma, ≥1,000 NIH units/mg protein, is preferred for the conversion of PEGylated fibrinogen to PEGylated fibrin.

In some embodiments, the microgel composition is composed of milled particles of fibrinogen or fibrin that are crosslinked with di- to multi-functional PEGylating agents, creating water-insoluble gel particles composed of various combinations of poly(ethylene glycol) substituents between, predominantly, pendant amino groups between the fibrinogen or fibrin protein chains. Each microgel particle is a composite of a multitude of protein chains of fibrinogen or fibrin, interspersed between shorter, but more numerous, poly(ethylene glycol) chains. Formation of the microgel particles occurs prior to application to tissue, organs, wounds, and tissue substitutes, which avoids in situ instrumentation for polymerization, provides the ability to remove contaminating monomers and initiators prior to introduction to the body, and avoid the generation of polymerization heat at the introduction site. This combination helps facilitate success of injection.

PEGylation of protein substituents and/or protein-based macromolecules can be done at molar ratios of 100:1, 75:1, 50:1, 35:1, 20:1, 15:1, 10:1, 7.5:1, 5:1, 2.5:1 and 1:1 of PEGylating agent to protein component, or any range starting from or ending with any of these molar ratios (e.g., 100:1 to 1:1, or 50:1 to 2.5:1, or 50:1 to 10:1, or 35:1 to 5:1). In some embodiments, molar ratios of PEGylating agent to protein component are 10:1, 20:1, 35:1, and 50:1. In some embodiments, after lyophilizing the monolithic gels, the freeze-dried polymers are powdered by mortar and pestle or by cryomilling, and further separated by sieving, giving median particle sizes of the dried microgel particles ranging from 10 µm to 1,000 µm, or from 50 µm to 500 µm, or from 75 µm to 250 µm. In some embodiments, after lyophilizing the monolithic gels, the freeze-dried polymers are powdered by mortar and pestle or by cryomilling, giving median particle size lengths of the dried particles ranging from 10 µm to 1,000 µm, or from 50 µm to 500 µm, or from 75 µm to 250 µm.

In some embodiments, the microgel particles are hydrated with a fluid. In some embodiments, the mobile phase of the fluid is water, isotonic saline, balanced salt solution, buffer solution, Ringer's solution, cell culture media, stem cell media, serum, plasma, amniotic fluid, Wharton's jelly, nutrient broth, antiseptic solutions, or a combination thereof. The degree of hydration of the microgel particles is dependent upon at least the molar ratio of PEGylating agent to derivatized protein, the degree of porosity, and surface area of the resulting microgel particles, and the pH, osmolality, and temperature of the mobile phase. In some embodiments, where the fluid is an aqueous media, the aqueous media can have a pH in the range 4.5-8.0, or 5.5 to 7.5. In some embodiments the degree of hydration (swelling) of the microgel particles can be at least 50 times, at least 40 times, at least 30 times, at least 20 times, at least 10 times, at least 5 times, or at least 2 times the dry weight of the microgel particle, when measured using saline solution.

In some embodiments, an antimicrobial agent is added to the microgel particles to hinder development and proliferation of microorganisms. In some embodiments, addition of an antimicrobial agent helps reduce or eliminate microbial colonies and biofilm formation. Because of the possibly of infection in voids, wounds, and burns, the PEGylated protein microgel composition can include a biological agent in an amount sufficient to hinder or eradicate microorganisms.

Examples of biological agents include, but are not limited to, antibiotics, antiseptics, anti-infective agents, antimicrobial agents, antibacterial agents, antifungal agents, antiviral agents, antiprotozoal agents, sporicidal agents, and antiparasitic agents. In some embodiments, the biological agent is biodegradable, non-cytotoxic to human and animal cells, or both biodegradable and non-cytotoxic.

Examples of biocidal agents include, but are not limited to, biguanides, such as poly(hexamethylene biguanide) (PHMB) and its salts, a low molecular weight synthetic cationic biguanide polymer, chlorhexidine and its salts, such as chlorhexidine digluconate, and alexidine and its salts, such as alexidine dihydrochloride, where the latter two are bis(biguanides), benzalkonium chloride, benzethonium chloride, cetyltrimethylammonium bromide, glycerol monolaurate, capryl glycol, gentamicin sulfate, iodine, povidone-iodine, starch-iodine, neomycin sulfate, polymyxin B, bacitracin, tetracyclines, clindamycin, gentamicin, nitrofurazone, mafenide acetate, silver nanoparticles, silver sulfadiazine, silver nitrate, terbinafine hydrochloride, miconazole nitrate, ketoconazole, clotrimazole, itraconazole, metronidazole, antimicrobial peptides, polyquaternium-1, polyquaternium-6, polyquaternium-10, salts thereof, and combinations thereof.

In some embodiments, the antimicrobial biguanide is poly(hexamethylene biguanide) hydrochloride (PHMB). PHMB can be used because of its high biocidal activity against microorganisms, combined with its biodegradation and low cytotoxicity. PHMB is primarily active against Gram negative and Gram positive bacteria, fungi, and viruses. In contrast to antibiotics, which are considered regulated pharmaceutical drugs and to which bacterial resistance can occur, such resistance does not occur with PHMB. As used herein, an "antimicrobial agent" is a substance that kills microorganisms or inhibits their growth or replication, while an "anti-infective agent" is a substance that counteracts infection by killing infectious agents, such as microorganisms, or preventing them from spreading. Often, the two terms are used interchangeably. As used herein, "PHMB" is considered an antimicrobial agent.

In some embodiments, the compositions containing hydrated or rehydrated PEGylated protein microgel particles described herein can include biocidal PHMB at a concentration ranging from 0.0001 wt % (1 ppm) to 1 wt % (10,000 ppm), or ranging from 0.01 wt % (100 ppm) to 0.75 wt % (7,500 ppm), or ranging from 0.05 wt % (500 ppm) to 0.5 wt % (5,000 ppm), or ranging from 0.1 wt % (1,000 ppm) to 0.25 wt % (2,500 ppm), based on the total weight of the composition. In some embodiments, dry PEGylated protein microgel particle compositions described herein can include biocidal PHMB at a concentration ranging from 0.002 wt % (20 ppm) to 25.0 wt % (250,000 ppm), or ranging from 0.20 wt % to 15.0 wt % (150,000 ppm), or ranging from 1.0 wt % (10,000 ppm) to 10.0 wt % (100,000 ppm), or ranging from 2.0 wt % (20,000 ppm) to 4.0 wt % (40,000 ppm), based on the total weight of the composition.

In some embodiments, bis(biguanide)s, such as alexidine and its salts and chlorhexidine and its salts, can be added to the antimicrobial PEGylated protein microgel particle compositions in concentrations from 0.001 wt % (10 ppm) to 4.0 wt % (40,000 ppm).

In some embodiments, surfactant-type antimicrobial agents, such as benzethonium chloride or benzalkonium chloride, can be added to the antimicrobial PEGylated protein microgel particle compositions in concentrations from 0.001 wt % (10 ppm) to 2.0 wt % (20,000 Ppm).

In some embodiments, lipophilic-type antimicrobial agents, such as glycerol monolaurate or capryl glycol, can be added to the antimicrobial PEGylated microgel particle protein compositions in concentrations from 0.1 wt % (1,000 ppm) to 2.0 wt % (20,000 ppm).

In some embodiments, antimicrobial agents with reactive functional groups, such as amino, imino, imidazoyl, sulfhydryl, hydroxyl, phenolic, indolyl, guanidium, guanidinium, and carboxyl groups, may be covalently incorporated into the PEGylated protein microgel particle, forming a ternary composite of PEGylated protein/antimicrobial agent. In some embodiments, covalently bound ternary composites of PEGylated fibrinogen/PHMB microgel particles are formed.

In some embodiments, aqueous PEGylated protein microgel particle compositions can have an osmolality of 10-340 mOsm/kg. In some embodiments where the PEGylated protein microgel particle composition is an aqueous-based solution, gel, paste, emulsion, or foam, a water-soluble polymer can be added to increase solution viscosity and to prolong residence time on the surface of a tissue, void, or wound, or subcutaneously in a void or wound. In some embodiments, useful water-soluble polymers include, but are not limited to, poly(ethylene glycol), poly(ethylene oxide), poly(vinyl alcohol) and copolymers, poly(N-vinylpyrrolidone) and copolymers, methylcellulose, hydroxyethylcellulose, hydroxypropylcellulose, hydroxypropylmethylcellulose, carboxymethylcellulose, guar gum, hydroxyethylguar, hydroxypropylguar, gelatin, albumin, hydroxypropylmethylguar, carboxymethylguar, carboxymethylchitosan, locust bean gum, carrageenan, xanthan gum, gellan gum, pullulan, alginate, chondroitin sulfate, dextran, dextran sulfate, Aloe vera gel, scleroglucan, schizophyllan, gum arabic, tamarind gum, poly(methyl vinyl ether), ethylene oxide-propylene oxide-ethylene oxide block copolymers, hyaluronan, chondroitin sulfate, keratan sulfate, dermatan sulfate, heparan sulfate, dextran, Carbomer and its salts, poly(acrylic acid) and its salts, poly(methacrylic acid) and its salts, poly(ethylene-co-acrylic acid), poly(vinyl methyl ether), poly(vinylphosphoric acid) salts, poly(vinylsulfonic acid) salts, sodium poly(2-acrylamido-2-methylpropanesulfonate), polyacrylamide(s), poly(N,N-dimethylacrylamide), poly(N-vinylacetamide), poly(N-vinylformamide), poly(2-hydroxyethyl methacrylate), poly(glyceryl methacrylate), poly(2-ethyl-2-oxazoline), poly(N-isopropylacrylamide) and poly(N-vinylcaprolactam), the latter two hydrated below their Lower Critical Solution Temperatures, polyquaternium-1, polyquaternium-6, polyquaternium-10, ionene polymers, cationic guar, pyridinium polymers, imidazolium polymers, diallyldimethylammonium polymers, poly(L-lysine), acryloyl-, methacryloyl-, and styryl-trimethylammonium polymers, acrylamido- and methacrylamido-trimethylammonium polymers, antimicrobial peptides, and the like, and derivatives and combinations thereof.

In some embodiments, the preparation of PEGylated protein microgel particle compositions in the form of viscous solutions, gels, creams, pastes, emulsions, balms, and sprays, can be facilitated by the inclusion of water-soluble polymer viscosity builders in amounts ranging from about 0.01 to about 50.0 wt %, from 0.1 to 45% wt, from 0.5 to 25 wt %, or from 1.0 to 10.0 wt %.

In some embodiments, essential oils can be added to the microgel particle compositions as fragrance or aromatic agents, and/or as antimicrobial agents. Examples of essential oils useful in the microgel particle compositions described herein include, but are not limited to, thymol, menthol, sandalwood, camphor, cardamom, cinnamon, jasmine, lavender, geranium, juniper, menthol, pine, lemon, rose, eucalyptus, clove, orange, oregano, mint, linalool, spearmint, peppermint, lemongrass, bergamot, citronella, cypress, nutmeg, spruce, tea tree, wintergreen (methyl salicylate), vanilla, and the like. In some embodiments, the essential oils can be selected from thymol, sandalwood oil, wintergreen oil, eucalyptol, pine oil, and combinations thereof. In some embodiments, essential oils can be present in an amount ranging from 0% to 5 wt % based on the weight of the PEGylated protein microgel particle composition. In some embodiments, essential oils can be present in an amount of at least 0.1 wt %, or at least 0.25 wt %, or at least 0.5 wt %, based on the weight of the PEGylated protein microgel particle composition.

In some embodiments, chlorophyllin, a water-soluble semi-synthetic derivative of chlorophyll, may also be used to control wound odor and to provide anti-inflammatory properties. In some embodiments, chlorophyllin can be present in an amount ranging from 0% to 5 wt % based on the weight of the PEGylated protein microgel particle composition. In some embodiments, chlorophyllin can be present in an amount of at least 0.1 wt %, or at least 0.25 wt %, or at least 0.5 wt % based on the weight of the PEGylated protein microgel particle composition.

In some embodiments, the PEGylated protein microgel particle composition can also include wetting agents, buffers, gelling agents or emulsifiers. Other excipients could include various water-based buffers ranging in pH from 5.0-7.5, surfactants, silicones, polyether copolymers, vegetable and plant fats and oils, hydrophilic and hydrophobic alcohols, vitamins, monoglycerides, laurate esters, myristate esters, palmitate esters, and stearate esters. In some embodiments, the PEGylated protein microgel particle composition can be in a form including, but not limited to, liquid, gel, paste, cream, emulsion, combinations thereof, and the like. In some embodiments, the PEGylated protein microgel particle composition is lyophilized to a dry powder. The lyophilized PEGylated protein microgel particle composition may be used in powder form, or the powder may be further processed (e.g., rehydrated) into solutions, suspensions, creams, lotions, gels, pastes, emulsions, balms, sprays, foams, aerosols, films, or other formulations.

In some embodiments, the PEGylated protein microgel particles are in the form of nanoparticles, nanoshells, nanorods, and combinations thereof. In some embodiments, the dehydrated or lyophilized PEGylated protein microgel particles are in the form of nanoparticles, nanoshells, nanorods, and combinations thereof.

As used herein, "aqueous media" refers to a spectrum of water-based solutions including, but not limited to, homogeneous solutions in water with solubilized components, cell media solutions, buffer solutions, isotonic solutions, salt solutions, emulsified solutions, surfactant solutions, amniotic fluids, Wharton's jelly, serum, hydrophilic polymers, and viscous or gelled homogeneous or emulsified solutions in water.

As used herein, "surfactant" has its standard meaning and includes compounds that lower the surface tension (or interfacial tension) between two liquids or between a liquid and a solid and includes emulsifying agents, emulsifiers, detergents, wetting agents, and surface-active agents.

As used herein, "hydrophilic" has its standard meaning and includes compounds that have an affinity to water and can be ionic or neutral or have polar groups in their structure that attract water. For example, hydrophilic compounds can be miscible, swellable, adsorbable, or soluble in water, with a stationary contact angle with water of ≤90° in water at room temperature.

As used herein, "hydrophobic" refers to repelling water, being insoluble or relatively insoluble in water, and lacking an affinity for water with a stationary contact angle with water of ≥90° in water at room temperature. Hydrophobic compounds with hydrophilic substituents, such as vicinal diols, may form emulsions in water, with or without added surfactant, with the hydrophilic substituent at the water interface and the hydrophobic portion of the compound in the interior of the emulsion.

As used herein, "swellable" refers to materials that uptake, absorb and/or adsorb fluids to their functional groups, surfaces, pores, micropores, nanopores, holes, and interstitial networks.

As used herein, the term "PEGylation" pertains to modifying a protein or protein-based macromolecule by covalently attaching poly(ethylene glycol) (PEG) with reactive substituents to the protein's available reactive functional groups, such as amino groups or sulfhydryl groups, whereas "PEGylated" refers to a protein having a PEG substituent attached thereto.

As used herein, "proteins" is intended to include protein-based macromolecules and includes extracellular matrices, glycoproteins, structural proteins, fibrous proteins, enzymes, proteoglycans, natural polypeptides, synthetic polypeptides, globular proteins, membrane proteins, plasma proteins, peptides, oligopeptides, antimicrobial peptides, peptide hormones, chaperones, metalloproteins, hemoproteins, coagulation proteins, immune system proteins, ion channel proteins, cell adhesion proteins, neuropeptides, nucleoproteins, scleroproteins, chromoproteins, conjugated proteins, protein-protein complexes, protein-polysaccharide complexes, protein-lipid complexes, protein-enzyme complexes, protein-polymer complexes, motor proteins, mucoproteins, phosphoproteins, contractile proteins, transport proteins, signaling proteins, regulatory proteins, growth factors proteins, sensory proteins, defense proteins, storage proteins, receptor proteins, antibodies, recombinant proteins, fibrinogen, fibrin, thrombin, collagen, elastin, albumin, gelatin, keratin, laminin, and combinations thereof.

As used herein, "derivatized proteins" are protein components attached, bound, coordinated, or complexed with another material, such as other proteins, polysaccharides, oligosaccharides, glycosaminoglycans, lipids, phospholipids, liposomes, synthetic polypeptides, DNA, RNA, synthetic polymers, surfactants, metal atoms, nanoparticles, antimicrobial agents, antibiotics, drugs, salts thereof, and the like.

As used herein, a "hydrogel" is an insoluble polymeric network composed of normally water-soluble macromolecules that exist in a crosslinked or pseudo-crosslinked state by covalent, ionic, or physical interaction among macromolecular chains, where the insoluble network adsorbs at least 10% of its weight in water. A hydrogel may contain one or more hydrophilic, polymeric species.

As used herein, a "monolithic" hydrogel consists of a single, large network of crosslinked, hydrophilic polymer or polymers, which can be subdivided into smaller, crosslinked microgel particles.

As used herein, a "microgel" is a gelatinous, water-insoluble, hydrophilic particle ranging in length from 1 micrometer to 1,000 micrometers, with diameters of 1 micrometer to 1,000 micrometers or a dehydrated particle capable of exhibiting those properties.

As used herein, "microgel particles" are mixed particles of water-insoluble, water-swellable gel fragments that have varied shapes, including spherical, elliptical, angular, regular (organized) or irregular shapes, either hollow, microporous, mesoporous, macroporous, or with void spaces, or a combination thereof, depending on the method of formation.

As used herein, the phrase "microporous" refers to materials that have pore diameters less than 2 nm, "mesoporous" particles have pore diameters between 2 and 50 nm, and "macroporous" particles have pore diameters greater than 50 nm.

As used herein, "flowable" pertains to a volume of fluid or gel that is capable of flowing through a passageway of any given dimension, such as through a squeeze tube, pump, cannula, or syringe.

As used herein, "injectable" describes the ability of a solution, suspension, gel, emulsion, or microgel to pass through a hypodermic needle or cannula.

As used herein, a "Newtonian fluid" exhibits a viscosity that is independent of the shear conditions studied.

As used herein, a "non-Newtonian fluid" exhibits a viscosity that is dependent upon the shear conditions studied.

As used herein, "pseudoplastic" pertains to a fluid composition having a viscosity that decreases with increasing shear rate, that is, shear thinning.

As used herein "shear rate" (also called shear strain rate) is the rate of change of strain as a function of time.

As used herein, "loss modulus (G")" is a measure of the energy dissipated in a material under deformation (e.g., shear). G" is attributable to viscous flow, rather than elastic deformation. Loss modulus is also known as viscous modulus.

As used herein, "storage modulus (G')" is a measure of the energy stored in a material under deformation (e.g., shear). G' is attributable to elastic deformation. Storage modulus is also known as elastic modulus.

As used herein, "loss tangent" (also called tan delta, tan δ) is the tangent of the phase angle (δ), which is the ratio of the loss (viscous) modulus (G") to the storage (elastic) modulus (G'), that is, tan δ=G"/G'. The loss tangent is a useful quantifier of the presence and extent of elasticity in a fluid. Loss tangent values of less than unity indicate an elastic-dominant (i.e., solid-like) behavior and values greater than unity indicate a viscous-dominant (i.e., liquid-like) behavior.

As used herein, "biologically active agents" has its standard meaning and includes chemical or biological substances or formulations that beneficially affect human or animal health and well-being or is intended for use in the cure, mitigation, treatment, prevention, or diagnosis of infection or disease, or is destructive to or inhibits the growth of microorganisms.

As used herein, "antimicrobial agent" has its standard meaning and include a substance that kills microorganisms or inhibits their growth or replication, while an "anti-infective agent" is defined as a substance that counteracts infection by killing infectious agents, such as microorganisms, or preventing them from spreading. Often, the two terms are used interchangeably.

As used herein, "antibiotic" has its standard meaning and includes those substances that were originally produced by a microorganism or synthesized with active properties that can kill or prevent the growth of another microorganism. The term antibiotic is commonly used to refer to almost any prescribed drug that attempts to eliminate infection.

As used herein, "excipient" has its standard meaning and includes inert substances that form a vehicle, such as a liquid, fluid, or gel, that solubilizes or disperses a PEGylated protein microgel particle composition, which may include other added ingredients.

As used herein, "viscoelasticity" is the property of materials that exhibit both viscous and elastic characteristics when undergoing deformation.

As used herein, "viscoelastic solids" are able to return to their original shape when an applied shear load is removed, while viscoelastic fluids do not.

As used herein, "soft tissue" has its standard meaning and includes biological tissue that connects, supports, or surrounds other structures and organs of the body, but does not include bone. Examples of soft tissue include tendons, ligaments, fascia, skin, fibrous tissues, fat, synovial membranes, muscles, nerves and blood vessels.

As used herein, "nanoparticles" are particles between 1 and 500 nanometers in size and also include particles between 1 and 100 nanometers in size.

As used herein, "nanoshells" are spherical cores of a particular compound surrounded by a shell or outer coating of another, which are a few nanometers thick.

As used herein, "nanorods" are rod-shaped particles that have a length at least twice a radius or width and are typically 1 to 100 nm in length.

As used herein, "microparticles" are particles of various dimensions between 0.1 and 100 μm in size.

As used herein, "microspheres" are spherical particles, with diameters typically 1 μm to 1,000 μm. Microspheres are sometimes referred to as microparticles.

In some embodiments, one or more observational or detectable agents may be incorporated into the PEGylated protein microgel particle composition to provide enhanced visualization or facilitate proper placement. The agents may comprise, in other embodiments, dyes, fluorescent substances, ultraviolet absorbers, radioactive substances, pigments, or any combinations thereof.

In some embodiments, one or more biologically active agents may be incorporated into the PEGylated protein microgel particle composition to provide a medical benefit to a mammalian host. Examples of biologically active agents that can be incorporated into the PEGylated protein microgel particle composition include, but are not limited to, cells, stem cells, amniotic tissue, amniotic cells, growth factors, micronized decellularized skin tissue, granulated cross-linked bovine tendon collagen and glycosaminoglycans, antibiotics, antiseptics, anti-infective agents, antimicrobial agents, antibacterial agents, antifungal agents, antiviral agents, antiprotozoal agents, sporicidal agents, antiparasitic agents, peripheral neuropathy agents, neuropathic agents, chemotactic agents, analgesic agents, anti-inflammatory agents, anti-allergic agents, anti-hypertension agents, mitomycin-type antibiotics, polyene antifungal agents, antiperspirant agents, decongestants, anti-kinetosis agents, central nervous system agents, wound healing agents, anti-VEGF agents, anti-tumor agents, escharotic agents, anti-psoriasis agents, anti-diabetic agents, anti-arthritis agents, anti-itching agents, antipruritic agents, anesthetic agents, anti-malarial agents, dermatological agents, anti-arrhythmic agents, anti-convulsants, antiemetic agents, anti-rheumatoid agents, anti-androgenic agents, anthracyclines, anti-smoking agents, anti-acne agents, anticholinergic agents, anti-aging agents, antihistamines, anti-parasitic agents, hemostatic agents, vasoconstrictors, vasodilators, thrombogenic agents, anti-clotting agents, cardiovascular agents, angina agents, erectile dysfunction agents, sex hormones, growth hormones, isoflavones, integrin binding sequence, biologically active ligands, cell attachment mediators, immunomodulators, tumor necrosis factor alpha, anti-cancer agents, antineoplastic agents, anti-depressant agents, antitussive agents, antineoplastic agents, narcotic antagonists, anti-hypercholesterolaemia agents, apoptosis-inducing agents, birth control agents, sunless tanning agents, emollients, alpha-hydroxyl acids, manuka honey, topical retinoids, hormones, tumor-specific antibodies, antisense oligonucleotides, small interfering RNA (siRNA), anti-VEGF RNA aptamer, nucleic acids, DNA, DNA fragments, DNA plasmids, Si-RNA, transfection agents, vitamins, essential oils, liposomes, silver nanoparticles, gold nanoparticles, drug-containing nanoparticles, albumin-based nanoparticles, chitosan-containing nanoparticles, polysaccharide-based nanoparticles, dendrimer nanoparticles, phospholipid nanoparticles, iron oxide nanoparticles, bismuth nanoparticles, gadolinium nanoparticles, metallic nanoparticles, ceramic nanoparticles, silica-based nanoparticles, virus-based nanoparticles, virus-like nanoparticles, antibiotic-containing nanoparticles, nitric oxide-containing nanoparticles, nanoshells, nanorods, polymeric micelles, silver salts, zinc salts, quantum dots nanoparticles, polymer-based microparticles, polymer-based microspheres, drug-containing microparticles, drug-containing microspheres, antibiotic-containing microparticles, antibiotic-containing microspheres, antimicrobial microparticles, antimicrobial microspheres, salicylic acid, benzoyl peroxide, 5-fluorouracil, nicotinic acid, nitroglycerin, clonidine, estradiol, testosterone, nicotine, motion sickness agents, scopolamine, fentanyl, diclofenac, buprenorphine, bupivacaine, ketoprofen, opioids, cannabinoids, enzymes, enzyme inhibitors, oligopeptides, cyclopeptides, polypeptides, proteins, prodrugs, protease inhibitors, cytokines, hyaluronic acid, chondroitin sulfate, dermatan sulfate, parasympatholytic agents, chelating agents, hair growth agents, lipids, glycolipids, glycoproteins, endocrine hormones, growth hormones, growth factors, differentiation factors, heat shock proteins, immunological response modifiers, saccharides, polysaccharides, insulin and insulin derivatives, steroids, corticosteroids, and non-steroidal anti-inflammatory drugs or similar materials, in either their salt form or their neutral form, either being inherently hydrophilic or encapsulated within a hydrophilic microparticle or nanoparticle. Such biologically active agents could be in either of the (R)-, (R, S)-, or (S)-configuration, or a combination thereof.

As used herein, "injection" has its standard meaning and includes intradermal, subcutaneous, oral, intramuscular, submucosal, subcutaneous, intranasal, vaginal, buccal, intrathecal, epidural, intraparenchymal, ocular, subretinal, dental, intratumoral, intracardiac, intra-articular, intravenous, intracavernous, intraosseous, intraperitoneal, intra-abdominal, intrafascial, intraogan, and intravitreal procedures.

As used herein, injections may be made into cavities/voids created surgically, cavities/voids resulting from disease, and cavities/voids resulting from injury.

As used herein, "cell culture" has its standard meaning and includes the transfer of cells, tissues or organs from an animal or plant and their subsequent placement into an environment conducive to their survival and/or proliferation.

In some embodiments, the injectable PEGylated protein microgel particle composition may include cells. Examples of cells useful in the PEGylated protein microgel particle compositions described herein include, but are not limited to, fibroblasts, keratinocytes, neurons, glial cells, astrocytes, Schwann cells, dorsal root ganglia, adipocytes, endothelial cells, epithelial cells, chondrocytes, fibrochondrocytes, myocytes, cardiomyocytes, myoblasts, hepatocytes, tenocytes, intestinal epithelial cells, smooth muscle cells, stromal cells, neutrophils, lymphocytes, bone marrow cells, platelets, and combinations thereof. In some embodiments, the cells are eukaryotic or mammalian. In some embodiments, the cells are of human origin. In some embodiments, the cells may be autologous or allogeneic.

In some embodiments the injectable PEGylated protein microgel particle composition may include adult stem cells, embryonic stem cells, amniotic stem cells, induced pluripotent stem cells, fetal stem cells, tissue stem cells, adipose-derived stem cells, bone marrow stem cells, human umbilical cord blood stem cells, blood progenitor cells, mesenchymal stem cells, hematopoietic stem cells, epidermal stem cells, endothelial progenitor cells, epithelial stem cells, epiblast stem cells, cardiac stem cells, pancreatic stem cells, neural stem cells, limbal stem cells, perinatal stem cells, satellite cells, side population cells, multipotent stem cells, totipotent stem cells, unipotent stem cells, and combinations thereof. In some embodiments, the stem cells are mammalian. In some embodiments, the stem cells are of human origin. In some embodiments, the stem cells may be autologous or allogeneic.

In some embodiments, the injectable PEGylated protein microgel particle compositions described herein may be used as a scaffold matrix to deliver a therapeutically effective amount of between 10,000 cells to about 1 billion cells.

In some embodiments, products derived from placental tissue may be incorporated with the PEGylated protein microgel particle composition for injection into a mammalian host. Placental tissues are a source of collagen, elastin, fibronectin, and growth factors, including platelet-derived growth factor (PDGF), vascular endothelial growth factor (VEGF), epidermal growth factor (EGF), fibroblast growth factor (FGF), and transforming growth factor beta (TGF-β), which can support tissue repair and regeneration. In particular, amniotic tissue has anti-adhesive and antimicrobial properties, and such tissue has been shown to support soft tissue repair, reduce inflammation and minimize scar tissue formation, which are significant benefits in the treatment of soft tissue injuries.

Amniotic tissues have been described as being immune-privileged in that an immune response in the human body rarely occurs in response to the introduction of amniotic tissue. In some embodiments a morselized, flowable tissue allograft derived from amniotic tissues, available from BioD, LLC, commercialized as BioDRestore™ Elemental Tissue Matrix, can be added to the PEGylated protein microgel particle composition for a coating or injection into soft tissue, or placement surrounding a tissue substitute. For example, PEGylated fibrinogen microgel particle compositions can include morselized, flowable tissue allograft derived from amniotic tissues.

In some embodiments, the PEGylated protein microgel particle composition may include growth factors. Examples of useful growth factors include, but are not limited to, epidermal growth factor (EGF), transforming growth factor beta (TGF-beta), fibroblast growth factor (FGF), vascular endothelial growth factor (VEGF), granulocyte macrophage colony stimulating factor (GM-CSF), platelet-derived growth factor (PDGF), connective tissue growth factor (CTGF), insulin-like growth factor (IGF), keratinocyte growth factor (KGF), interleukin (IL) family, stromal cell derived factor (SDF), heparin binding growth factor (HBGF), nerve growth factor (NGF), brain-derived neurotrophic factor (BDNF), growth differentiation factor (GDF), muscle morphogenic factor (MMF), and tumor necrosis factor-alpha (TNFα).

In some embodiments, the multi-component PEGylated protein microgel particle composition can be used as an injectable soft tissue void filler and may also include any other component suitable for augmenting, strengthening, supporting, repairing, rebuilding, healing, occluding or filling a soft tissue.

The flow properties of the hydrated microgel particle compositions can be determined by rheometry, wherein the storage modulus (G') and loss modulus (G") of biologically weak (soft) materials, such as ocular tissues (vitreous) and fat, are substantially lower than related values for strong materials, such as muscle, tendon, and cartilage. In this regard, values of G' range from 1 Pa to 1 MPa and values of G" range from 0.1 Pa to 1 MPa, which include properties of the particular hydrated microgel particle composition (e.g., individual microgel particles and clusters of microgel particles, whether alone or with free liquid or solid components) In some embodiments, the storage modulus for the PEGylated protein microgel particle compositions described herein ranges from 10 Pa to 250,000 Pa, from 50 Pa to 175,000 Pa, and from 100 Pa to 100,000 Pa. In some embodiments, the loss modulus ranges from 5 Pa to 100,000 Pa, from 7.5 Pa to 50 Pa, and from 10 Pa to 10,000 Pa. The crosslinked, hydrated, PEGylated microgel particles display pseudoplasticity under shear, with viscosity decreasing with increasing shear rate. This pseudoplastic phenomenon is based on the water-insoluble, hydrated particles themselves and not on the fluid medium containing soluble macromolecules. Additionally, the rheological behavior of the microgel particle compositions, including the individual and clustered microgel particles, described herein are surprisingly related to their solid-like behavior, as opposed to being more fluid-like, as demonstrated by loss tangent values (G"/G') less than 1.

Also disclosed are uses of the compositions described herein for treating a soft tissue lesion or injury. Any of the compositions described herein can be used. In particular, the compositions can be used for injection into soft tissue. The injection can be intradermal, subcutaneous, oral, intramuscular, submucosal, intranasal, vaginal, buccal, intrathecal, epidural, intraparenchymal, ocular, subretinal, dental, intratumoral, intracardiac, intra-articular, intravenous, intracavernous, intraosseous, intraperitoneal, intra-abdominal, intrafascial, intraogan, and intravitreal. In some embodiments, the water-insoluble, microgel particles of the compositions described herein are in the form of a dry powder, and the use and or method further comprises hydrating said dry powder prior to said injection step. In such embodiments, after injection, the composition promotes angiogenesis.

EXPERIMENTAL

The following materials and abbreviations are used in the Experimental section:

ADSC: Adipose derived stem cells, primary human abdominoplasty cells.

AHF: Cryoprecipitated antihemophilic factor, South Texas Blood & Tissue Center, Lot W1409114 212930.
BSA: Bovine serum albumin, bioWORLD, 22070004-1, Lot V11121401.
Calcium Chloride: Sigma C4901, Lot 110M0105V.
Carbopol: Lubrizol, Carbopol® Aqua SF-2, Lot 0101014502.
Collagen Type I: Corning Incorporated, Product 354236, rat tail tendon, Lot 3298599.
ECM: Extracellular matrix, Engelbreth-Holm-Swarm murine sarcoma, Sigma E1270, Lot 093M4006V.
Gellan Gum: CP Kelco, Kelcogel CG-LA, Lot 1E0566A.
Guar Gum: Making Cosmetics, Lot 1092118.
Human Fibrinogen (FGN): Sigma F3879, Lots 061M7010, 071M7032V, SLBH0223V, SLBK3747V.
Human Thrombin: Sigma T7009, Lots 041M7007V, 011M7009V, SLBB4394V.
Hydroxyethyl Cellulose, Cationic: Dow Chemical Company, UCare™ Polymer JR-30M, Lot XL2850GRXA.
Hydroxypropylmethylcellulose: Amerchol Methocel K15M, Lot WF15012N01.
Morselized Amnion: BioD, LLC, BioDRestore™, Tissue ID R0925131.
NaOH: Sodium hydroxide, Puritan Products 7705, Lot 011043.
Needle: 18 G, BD 305195, Lot 2089215.
PBS: Phosphate Buffered Saline: pH 7.8-8.0 (without calcium and magnesium), INCELL ZSOL:F, Lots A2014SEP10-01, Z2015JAN05-01; or Sigma-Aldrich D8537, Lots RNBB9451, RNBC1143, RNBC8400.
PHMB: Poly(hexamethylene biguanide) Hydrochloride: Arch Chemicals, Cosmocil CQ™, Lots 9PL211280, 137261 or Lotioncrafter Biguanide 20, Lot 14RC169159-6380.
Poly(ethylene glycol) Diacrylate: MW 575, Sigma-Aldrich 437441, Lot MKBN7800V.
Poly(vinyl alcohol): DuPont, Elvanol®, Lot 910113.
PSG-(PEO)$_4$: Pentaerythritol tetra(succinimidyloxyglutaryl) polyoxyethylene, 4arm (tetrafunctional), NOF America Corporation, Sunbright® PTE-050GS (MW 5,000), Lot M8N526; PTE-100GS (MW 10,000), Lot M9D105; and PTE200-GS (MW 20,000), Lot M119691.
Pullulan: Hayashibara, Lot 1G3021.
SG-PEG-SG (PEG): NOF America Corporation, α-Succinimidyloxyglutaryl-ω-succinimidyloxyglutaryloxypolyoxyethylene, (difunctional), NOF America Corporation; Sunbright® DE-034GS (MW 3400), Lot M83541; DE-100GS (MW 10,000), Lot M107543; DE-200GS (MW 20,000), Lot M115700.
SG-PEG: α-Succinimidyloxyglutaryl-ω-methoxypolyoxyethylene, (monofunctional), NOF America Corporation, Sunbright® ME-050GS (MW 5,000), Lot M10N587.
Xanthan Gum: Bob's Red Mill, Lot 143454.
Protocols for Initial Hydrogel Formation:

Example 1: Poly(Ethylene Glycol)-Human Fibrinogen (PEG-FGN)

The preparation of various molar ratios of PEGylated fibrinogen (PEG-fibrinogen, PEG-FGN) is illustrated by the preparation of 20:1 molar PEG-FGN. Fibrinogen (FGN, MW 340 kDa) was dissolved at 80 mg/mL in sterile pH 7.8-8.0 PBS (without calcium and magnesium). The fibrinogen was dissolved at room temperature or 37° C. SG-PEG-SG (MW 3.4 kDa) was dissolved at 16 mg/mL in sterile pH 7.8-8.0 PBS (without calcium and magnesium) at room temperature (~22° C.). All lots of fibrinogen tested performed similarly. The reactive difunctional PEG solution of SG-PEG-SG was sterile filtered with a 0.20-0.22 µm filter. The SG-PEG-SG was then blended with FGN at 1:1 v/v (equivolume). Gelation occurred within 5-30 minutes at room temperature or at 37° C.

PEG-FGN was also prepared at molar ratios of 10:1, 35:1, or 50:1. It has been determined that lower levels of PEGylation results in a higher concentration of fibrinogen incorporation (more bioactive in the scaffold matrix), increases ease of manufacturing (more PEG retains more water, making lyophilization more difficult, and making milling in small particles very difficult), and preferential adhesion and proliferation in vitro of adipose derived stem cells (ADSC) on the 20:1 PEG-FGN scaffold compared to 35:1 and 50:1 PEG-FGN scaffolds.

PEG-FGN was also prepared at a molar ratio of 20:1 using the following PEGylating agents:
PEG Diacrylate (difunctional);
SG-PEG-SG, Sunbright DE-034GS (MW 3400), DE-100GS (MW 10,000), DE-200GS (MW 20,000) (difunctional);
SG-PEG: Sunbright® ME-050GS (MW 5,000) (monofunctional);
PSG-(PEO)$_4$, PTE-050GS (MW 5,000), Sunbright PTE-100GS (MW 10,000), PTE200-GS (MW 20,000) (tetrafunctional);
where
DE: NHS—OCO(CH$_2$)$_3$COO-PEG-CO(CH$_2$)$_3$COO—NHS;
ME: PEG-CO(CH$_2$)$_3$COO—NHS;
PTE: PEG-(CO(CH$_2$)$_3$COO—NHS)$_4$; and
NHS: N-Hydroxysuccinimide.

Increasing the molecular weight of the PEGylating agent yielded a firmer gel. Difunctional PEG produced stiff gels, in comparison to monofunctional PEG, which produced a fluid. Increasing the functionality of the PEG produced stiffer gels at the same molar ratios. PEG diacrylate did not form a gel under the reaction conditions studied.

Example 2: PEG-FGN-PHMB

PEG-FGN hydrogels (20:1 molar) were prepared with the addition of PHMB present in amounts ranging from 0 to 1000 ppm. The preparation of PEG-FGN-PHMB composites is illustrated by the incorporation of 100 ppm PHMB (concentration where the microgel is rehydrated at 50 mg/mL), with other concentrations of PHMB being prepared analogously.

PHMB was diluted in sterile pH 7.8-8.0 PBS without calcium and magnesium. The calculated amount of the PHMB solution to be added was based upon 0.01% w/w PHMB in the final rehydrated powder (powdered product is rehydrated at 50 mg/mL). This requires incorporation in the initial hydrogel of 48 µL PHMB solution per 100 mL total gel volume. For a 100 mL batch, 0.048 mL (48 µL) PHMB (Cosmocil CQ) was added to 50 mL phosphate buffered saline. The PEGylating agent was dissolved at 16 mg/mL in this dilute PHMB solution. Gel formation was initiated by addition of 50 mL of 80 mg/mL fibrinogen solution.

Example 3: PEG-FGN-Polymers

PEG-FGN-water soluble polymer hydrogels (20:1 molar PEG to FGN) were prepared with the incorporation of the following water-soluble polymers: Carbopol at 27.6 mg/mL, pullulan at 27.6 mg/mL, guar gum at 20.7 mg/mL, hydroxyethyl cellulose at 3.4 mg/mL, and collagen type I at 1.4 mg/mL. Carbopol is a crosslinked synthetic polymer based upon acrylic acid; pullulan and guar gum are natural polysaccharides; hydroxyethyl cellulose is a modified polysaccharide; and collagen type I is a protein, and the most abundant collagen of the human body. The water-soluble polymers were added prior to PEGylation.

Example 4: PEG-Fibrin

PEG-fibrin gels were prepared at molar ratios of 10:1 to 50:1. Increasing PEGylation beyond 20:1 molar hindered the activity of thrombin and the formation of fibrin gels, and longer reaction times were needed. Thrombin was added to PEG-fibrinogen for crosslinking of fibrinogen with thrombin concentrations of 2.5-12.5 U/mL gel.

The preparation of PEG-fibrin gels is illustrated for 10:1 molar PEG-fibrin with 2.5 U/mL thrombin. Fibrinogen (MW 340 kDa) was dissolved at 80 mg/mL in sterile pH 7.8-8.0 phosphate buffered saline (without calcium and magnesium). SG-PEG-SG (MW 3.4 kDa) was dissolved at 8 mg/mL in sterile pH 7.8-8.0 PBS (without calcium and magnesium) at room temperature. The reactive PEG solution was sterile filtered with a 0.20-0.22 μm filter. PEG was blended with FGN at 1:1 v/v (equivolume) and reacted 5 min (PEGylated fibrinogen solution). Thrombin (100 U/mL in deionized water) was diluted to 5 U/mL in 40 mM calcium chloride. PEG-fibrin gels were formed by mixing 1 part PEGylated fibrinogen solution with 1 part PBS and 2 parts 5 U/mL thrombin in calcium chloride. Gelation occurred within 5 minutes at room temperature or at 37° C.

PEG-fibrin was also prepared at molar ratios of 10:1, 35:1, or 50:1 with thrombin concentrations of 2.5-12.5 U/mL gel according to the above procedure. Previously, PEG-fibrin monolithic hydrogels at molar ratios of PEG to fibrinogen, converted to fibrin via thrombin, of 1:1, 2.5:1, 5:1, 7.5:1, 10:1, 15:1, 20:1, 100:1 have been reported (Zhang et al., Tissue Engineering, 12(1), 9-19, 2006).

Example 5: PEG-Fibrin-Polymers

PEGylated fibrin (10:1) hydrogels were prepared with the following water-soluble polymers incorporated at 2 mg/mL: xanthan gum, gellan gum, guar gum, cationic hydroxyethylcellulose, hydroxypropylmethylcellulose, and poly(vinyl alcohol). Xanthan gum, gellan gum and guar gum are naturally-occurring polysaccharides, cationic hydroxyethylcellulose and hydroxypropylmethylcellulose are modified polysaccharides, and poly(vinyl alcohol) is a synthetic vinyl-based polymer.

PEGylated fibrin (10:1) hydrogels were also prepared with the following polymers incorporated: Carbopol at 20 mg/mL, pullulan at 20 mg/mL, guar gum at 15 mg/mL, hydroxyethylcellulose at 2.5 mg/mL, and collagen type I at 1 mg/mL.

The hydrogels of PEG:Fibrin:polymers were prepared as follows: Fibrinogen was PEGylated by blending the PEGylating agent and fibrinogen at a molar ratio of 10:1. After PEGylating for 5 minutes, the water soluble polymer was added to the solution and then thrombin was added to initiate crosslinking.

Example 6: PEG-Proteins

The following proteins were PEGylated at a molar ratio of 20:1: fibrinogen, bovine serum albumin, collagen type I, Cryoprecipitated Antihemophilic Factor (AHF), and extracellular matrix using a procedure analogous to that of Example 1. PEGylation induced gel formation when the pH was increased to >7.0 with 1 M NaOH. For in vivo applications and protein stability, pH ranges from 6.6 to 8.0 can be used. The hydrated PEGylated gels were converted to microgel particles by rapid mechanical stirring. Pseudoplasticity of the resulting microgel particles was demonstrated by loading the hydrated microgel particles into a syringe and injecting the microgels with PBS through an 18 gauge needle, wherein a cluster of microgels formed as shear was removed.

Alternately, the following proteins were PEGylated at a molar ratio of 20:1: bovine serum albumin, collagen type I, and extracellular matrix. The hydrogels were dried, rehydrated, and mechanically blended to form microgels. Pseudoplasticity of the microgels was demonstrated by loading the resulting hydrated microgel particles into a syringe and injecting the microgel particles with PBS through an 18 gauge needle, wherein a cluster of microgels formed as shear was removed.

Protocols for Microgel Particle Formation

The PEGylated fibrinogen- and fibrin-based hydrogels were lyophilized 24-96 hours. Lyophilized gels were then milled using a mortar and pestle or Spex SamplePrep 6870 CryoMill (Metuchen, N.J.). Dry microgel powder could then be sieved to particle sizes (<250 μm, <150 μm, <106 μm, or <75 μm) using Tyler or Retsch stainless steel test sieves. The dried microgel powder was rehydrated with PBS (with and without calcium and magnesium), normal saline (0.9% sodium chloride), deionized water, cell culture media (with and without cells), or morselized amnion.

The process for microgel preparation is shown in FIG. 1 utilizing a crosslinked PEGylated fibrin with a PEG:fibrin molar content of 10:1, wherein the initial monolithic gel (Gelled PEG-fibrin) is lyophilized (Lyophilized PEG-fibrin), followed by grinding to a powder by cryomilling (Milled PEG-fibrin), and rehydrating to a microgel particles (Rehydrated PEG-fibrin). All microgel powders were prepared by this procedure.

Swelling Behavior of PEG-Fibrinogen and PEG-Fibrin Microgels

In Table 1 are presented the swelling behavior of microgel particles of 20:1 PEG-FGN and 10:1 PEG-fibrin. Swelling is determined on the basis of water-uptake from a dried microgel particle, that is, weight hydrated microgel/weight dry microgel. In comparison to the 50:1 formulations of PEG-FGN and PEG-fibrin, the fibrinogen formulation is more hydrophilic than the fibrin formulation. This is perhaps related to the additional crosslinking in PEG-fibrin because of the conversion of fibrinogen to fibrin by thrombin.

When water-soluble polymers were incorporated into 10:1 PEG-fibrin and 20:1 PEG-fibrinogen microgel particles, water uptake increased. Incorporation of these water-soluble hydrophilic polymers increased hydrophilicity of the microgel particle network, increasing the degree of swelling. Hydrophilic polymers examined include PHMB, Carbopol, pullulan, guar gum, hydroxyethyl cellulose (HEC), and type I collagen. PEG-fibrin gels contained Carbopol at 20 mg/mL, pullulan at 20 mg/mL, guar gum at 15 mg/mL, hydroxyethylcellulose at 2.5 mg/mL, and collagen type I at 1 mg/mL. PEG-FGN gels were prepared with Carbopol at 27.6 mg/mL, pullulan at 27.6 mg/mL, guar gum at 20.7 mg/mL, hydroxyethyl cellulose at 3.4 mg/mL, and collagen type I at 1.4 mg/mL.

TABLE 1

PEG-fibrin, PEG-fibrinogen microgel swelling and % hydration

| Formulation | Swelling | % Hydration |
| --- | --- | --- |
| PEG-fibrin 10:1 | 6.1 ± 0.6 | 86 |
| PEG-fibrin 20:1 | 7.3 ± 0.6 | 88 |
| PEG-fibrin 50:1 | 7.9 ± 1.0 | 89 |
| PEG-FGN 20:1 | 8.6 ± 1.1 | 90 |
| PEG-FGN 35:1 | 10.2 ± 0.7 | 91 |
| PEG-FGN 50:1 | 13.9 ± 1.4 | 93 |
| PEG-FGN-PHMB 100 ppm | 9.7 ± 0.4 | 91 |
| PEG-fibrin-Carbopol | 8.4 ± 1.8 | 89 |
| PEG-fibrin-Pullulan | 6.7 ± 0.1 | 87 |
| PEG-fibrin-Guar Gum | 8.4 ± 2.0 | 89 |
| PEG-fibrin-HEC | 11.4 ± 2.4 | 92 |
| PEG-fibrin-Collagen | 7.3 ± 0.5 | 88 |
| PEG-FGN-Carbopol | 11.8 ± 2.6 | 92 |
| PEG-FGN-Pullulan | 10.7 ± 2.8 | 91 |
| PEG-FGN-Guar Gum | 12.9 ± 3.5 | 93 |
| PEG-FGN-HEC | 11.4 ± 2.6 | 92 |
| PEG-FGN-Collagen | 9.1 ± 0.9 | 90 |

Rheological Behavior

Figure 2:
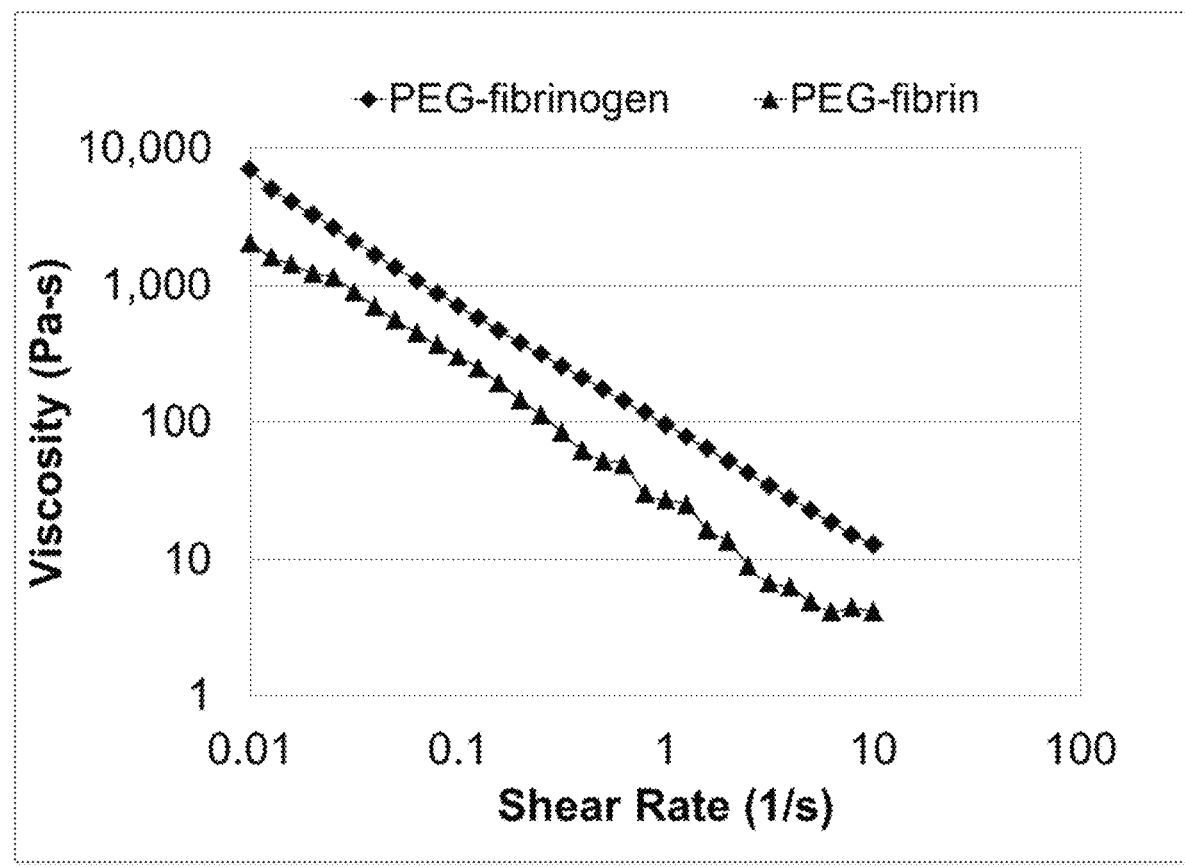
FIG. 2 is a graph showing the shear thinning behavior of a 10:1 molar ratio PEG-fibrin and 20:1 molar ratio PEG-fibrinogen microgels. The cryomilled microgels were rehydrated at 300 mg/mL in phosphate buffered saline. Values of slopes are as follows: PEG-fibrinogen (−0.90) and PEG-fibrin (−0.98). Slopes of approximately −1 indicate perfectly shear thinning materials.

It was determined that the hydrated microgel particles are shear thinning. This unexpected property makes them particularly useful for ease of fluid injection or placement at a specific site, and allows the microgel particle composition to act as a viscoelastic solid immediately after injection to maintain shape and conform to native surrounding tissue. A rheometer (Anton-Paar MCR 101 or Anton-Paar MCR 302, Ashland, Va.) was used to determine the pseudoplastic behavior and viscoelastic properties of the microgel particle compositions. Utilizing 20:1 molar ratio of rehydrated PEG-fibrinogen and 10:1 rehydrated PEG-fibrin microgel particles as examples made by cryomilling (or mortar and pestle), the viscosity vs. shear rate shown in FIG. 2 demonstrates that the crosslinked PEGylated protein microgel particle compositions rapidly shear thin, as illustrated by the absolute values of slopes of these plots, wherein the slope of PEG-fibrinogen is −0.90 and that of PEG-fibrin is −0.98, where a slope of approximately −1 indicates a perfectly shear thinning material.

Figure 3:
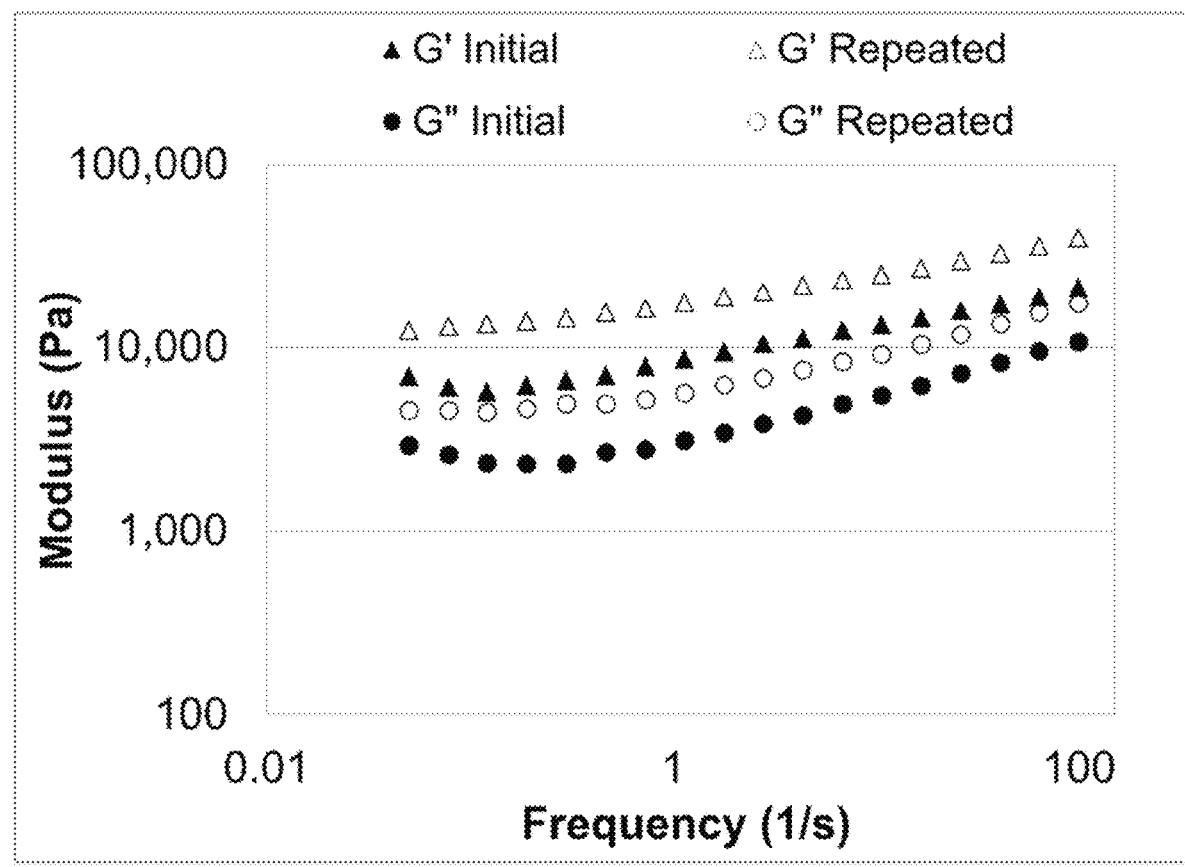
FIG. 3 is a graph of modulus vs. frequency for 20:1 PEG-fibrinogen microgel particles rehydrated at 300 mg/mL in phosphate buffered saline. Viscoelastic properties are recoverable after repeated exposure to 1% strain. The slightly higher storage and loss moduli for the repeated testing are an artifact of microgel dehydration over time.

For 20:1 PEG-fibrinogen as an example, the mechanical properties fully recover with no loss of viscoelasticity after repeated exposure to 1% strain (FIG. 3).

Figure 4:
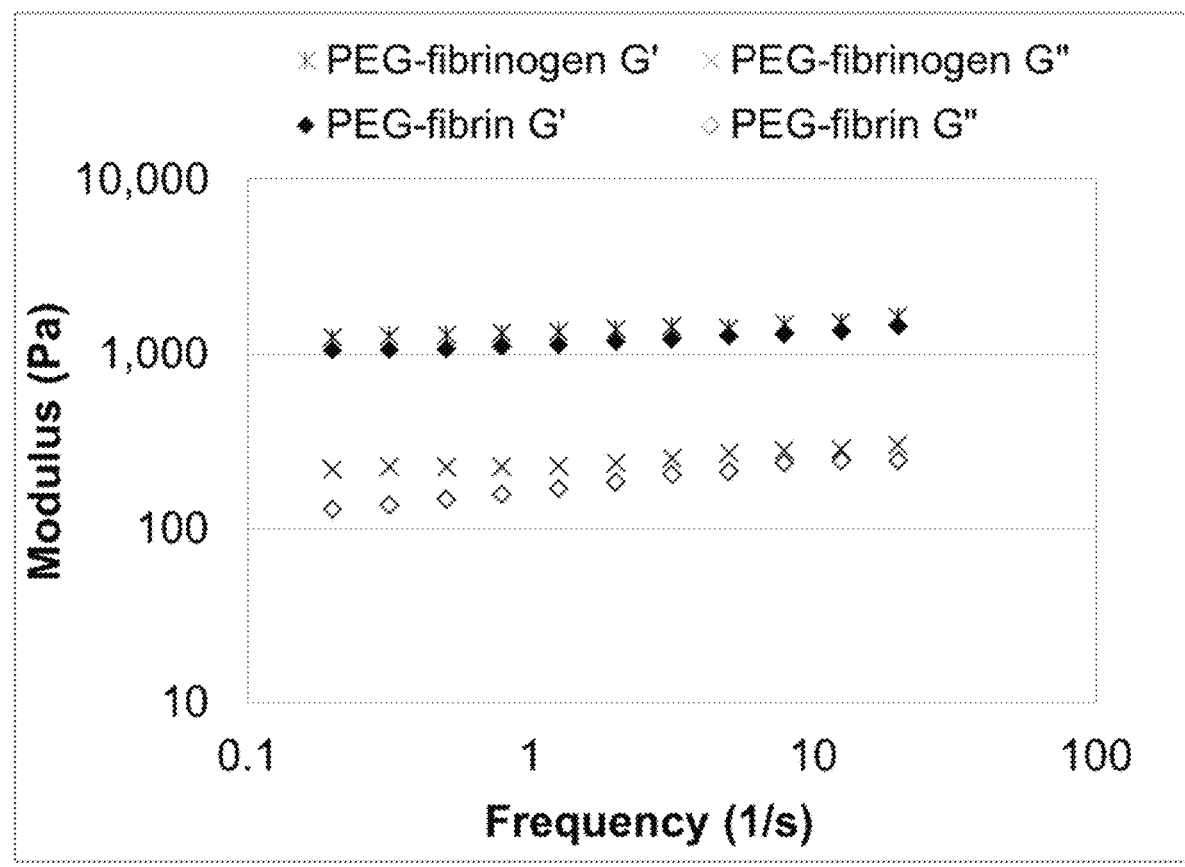
FIG. 4 is a graph comparing the storage (G') and loss (G") moduli of 10:1 PEG-fibrin and 20:1 PEG-fibrinogen microgels in a plot of modulus vs. frequency. The microgels were rehydrated at a concentration of 300 mg/mL in phosphate buffered saline.

Additionally, both PEG-fibrinogen and PEG-fibrin hydrated microgel particle compositions act as viscoelastic solids with storage moduli greater than loss moduli (FIG. 4, G'>G", or loss tangent <1) (Table 2).

TABLE 2

Loss Tangents for 10:1 PEG-fibrin, PEG-fibrinogen, and PEG-FGN-PHMB at a frequency of 1 1/sec

| Formulation | Loss Tangent |
| --- | --- |
| PEG-fibrin 10:1 | 0.18 |
| PEG-FGN 20:1 | 0.29 |
| PEG-FGN 35:1 | 0.22 |
| PEG-FGN 50:1 | 0.19 |
| PEG-FGN-PHMB 1000 ppm | 0.21 |

Figure 5:
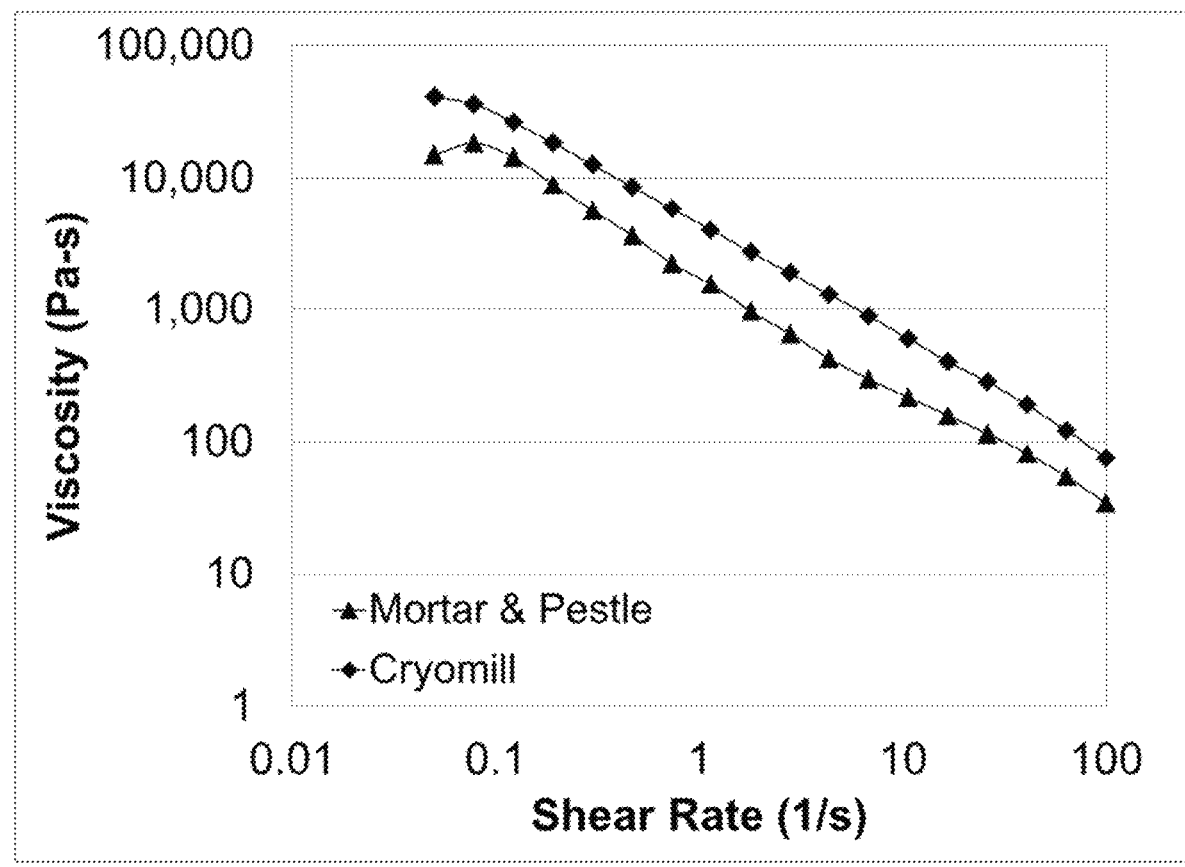
FIG. 5 is a graph of viscosity vs. shear rate showing the shear thinning behavior of 50:1 PEG-fibrinogen microgel particles milled by mortar & pestle as well as cryomilling. The microgels were rehydrated at 300 mg/mL in phosphate buffered saline.

The shear thinning behavior of 50:1 PEG-fibrinogen microgel milled by mortar and pestle and by cryomilling is shown in FIG. 5 for a plot of viscosity vs. shear rate. Dried microgel particles obtained by mortar and pestle were flatter and more flake-like, whereas dried particles obtained by cryomilling were more spherical. The microgels were rehydrated at 300 mg/mL in phosphate buffered saline. The slopes of the plots are −0.86 for mortar and pestle and −0.84 for cryomilling. The cryomilled particles were somewhat more viscous, presumably due to decreased particle size distribution and decreased average particle size.

Human Adipose-Derived Stem Cells

Human adipose-derived stem cells (ADSC) were isolated from human abdominal fat and subcultured in MesenPRO RS™ Medium (Life Technologies) with growth supplement and 1% penicillin-streptomycin. Powdered samples of PEG-FGN and PEG-fibrin, at 10:1, 20:1, and 50:1, (15 mg) were combined with 400 µL of $2.5 \times 10^5$ cells/mL suspension in cell culture inserts (transparent PET membrane size=8.0 µm, BD Biosciences) on a 12 well plate (n=3). Another 600 µL media was added to the insert and another 1 mL outside, resulting in 2 mL total media volume. The culture medium was exchanged daily and cell growth was examined using CellTiter 96® Aqueous One Solution Cell Proliferation Assay (MTS) (Promega) according to the manufacturer's protocol. Afterwards, cells were stained with Calcein AM (4 mM) live cell stain for 45 minutes and fixed with 10% formalin. The macroscopic and fluorescent image of each sample was acquired using a digital camera and confocal microscopy, respectively.

Figure 6:
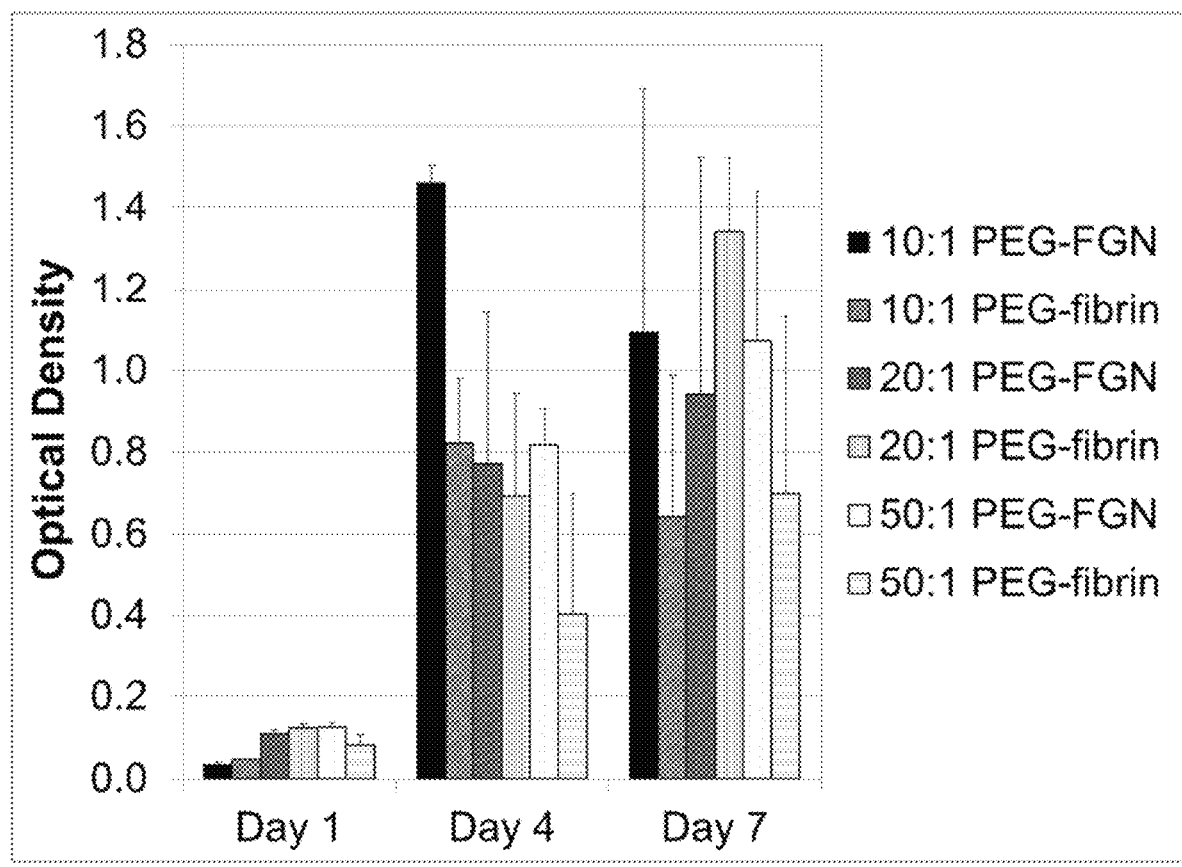
FIG. 6 is a chart showing the proliferation of adipose-derived stem cells (ADSC) on microgel particles of PEG-fibrinogen (PEG-FGN) and PEG-fibrin over 1, 4 and 7 days.
Figure 7:
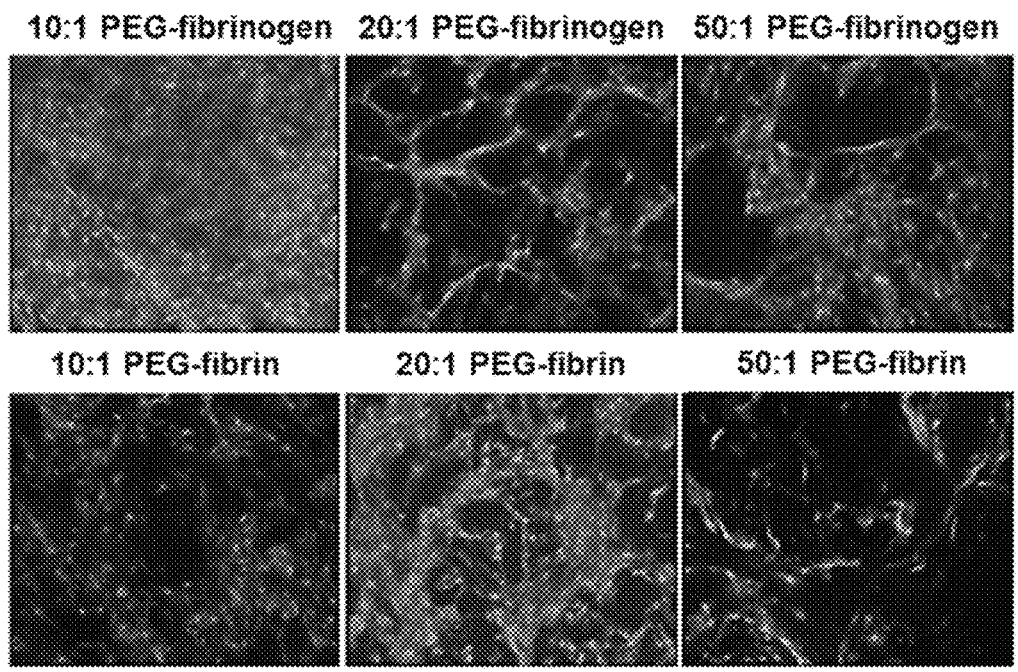
FIG. 7 shows live cell staining images for human ADSCs on 10:1, 20:1, and 50:1 PEG-fibrinogen and PEG-fibrin microgels on day 7, which demonstrates that the ADSCs are viable on 20:1 PEG-fibrinogen and 50:1 PEG-fibrinogen microgels.

FIG. 6 shows that the stem cells significantly increased in number on the microgels from day 1 to day 4. Cells continued to proliferate on the 20:1 and 50:1 formulations from day 4 to day 7. Live cell staining presented in FIG. 7 shows that the ADSCs are viable on all the microgel particle compositions tested. The cells appear to be forming networks on the 20:1 PEG-fibrinogen and 50:1 PEG-fibrinogen microgels.

Figure 8:
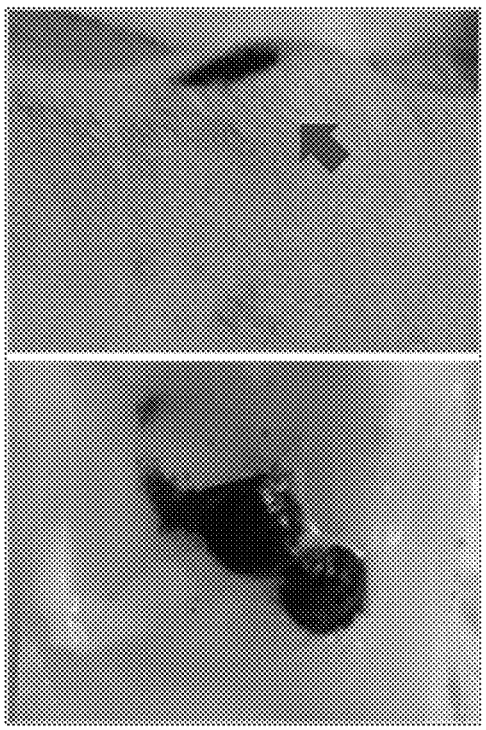
FIG. 8 shows images of the ex vivo subcutaneous injection (rat) of dyed 20:1 PEG-FGN microgels. The microgel acts as a solid after injection, retaining its shape and remaining at the site of injection.

Thus, a significant utilization of the microgel particle compositions is their ability to reform as a cluster of microgel particles after injection or movement by fluid. In FIG. 8 is shown 20:1 PEGylated fibrinogen microgels injected subcutaneously ex vivo in rats, wherein the microgel particles formed a cohesive solid and maintained their shape at the injection site.

Antimicrobial Properties

Figure 9:
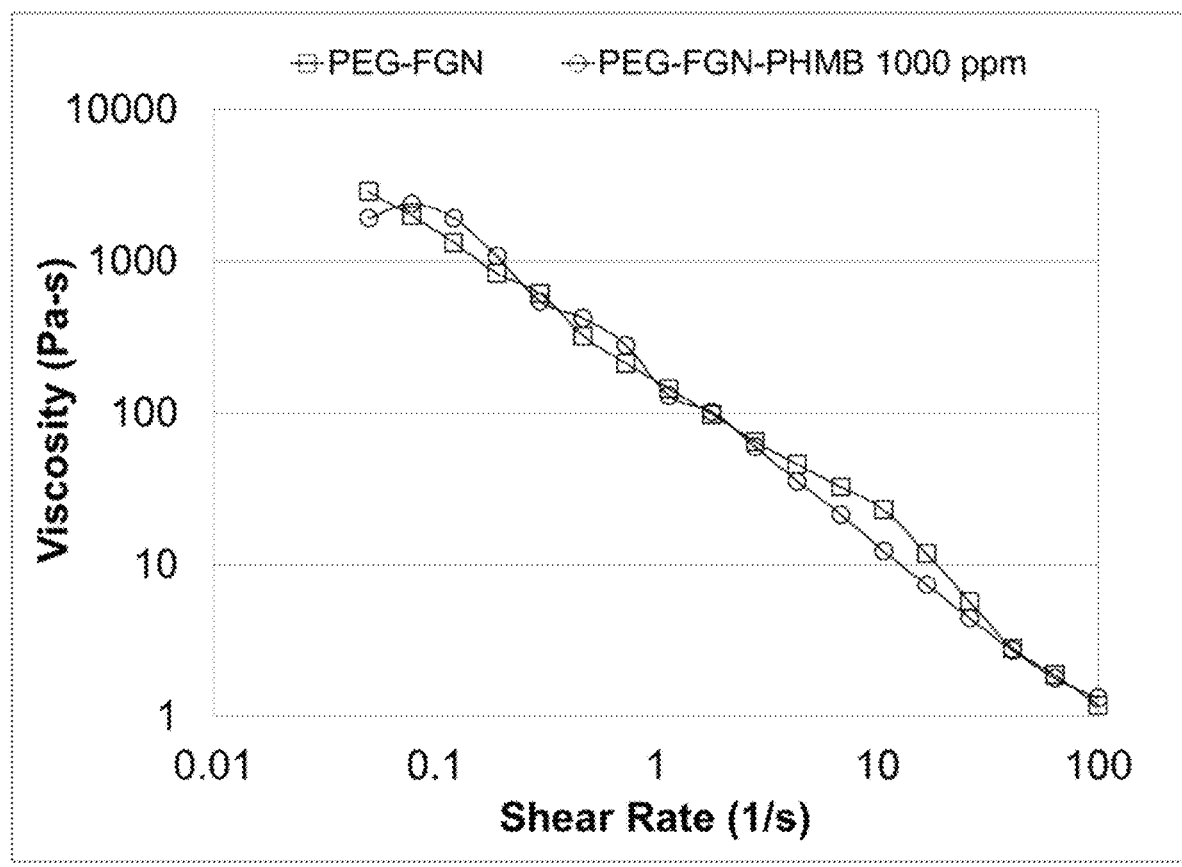
FIG. 9 is a graph of viscosity vs. shear rate showing the shear thinning behavior of 20:1 PEG-FGN gels without and with PHMB incorporated at rehydrated concentration of 1000 ppm PHMB. The microgels were rehydrated in phosphate buffered saline at 300 mg/mL.

In order to confer antimicrobial properties on the PEGylated microgel particle compositions, PHMB was incorporated into the PEGylation reaction with fibrinogen. FIG. 9 shows the pseudoplasticity of the ternary complex of 20:1 PEG-FGN-PHMB at 1,000 ppm of PHMB, in comparison to 20:1 PEG-FGN. The values of slopes are −1.01 for PEG-FGN and −1.06 for PEG-FGN-PHMB, with slopes of approximately −1 indicating perfectly shear thinning materials.

Figure 10:
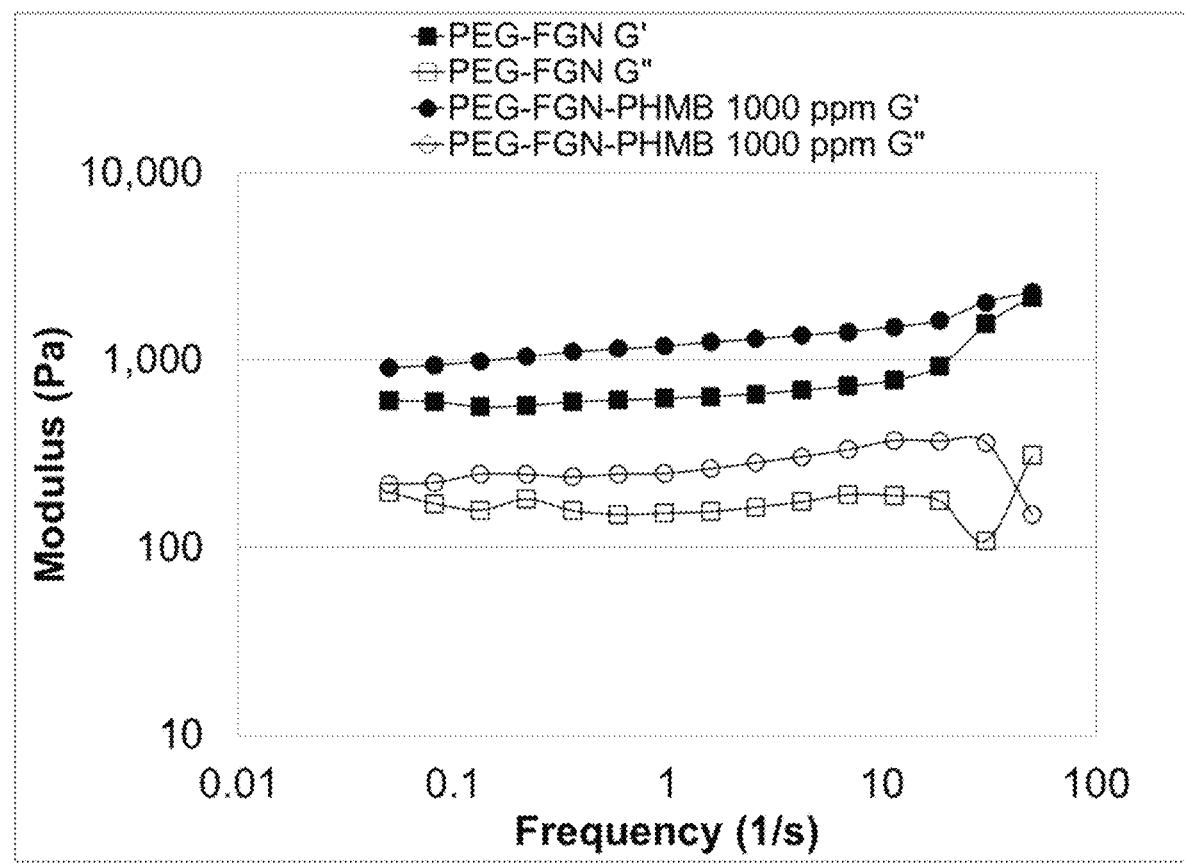
FIG. 10 is a graph of modulus vs. frequency showing the storage and loss moduli of 20:1 PEG-FGN gels without and with PHMB incorporated at rehydrated concentration (50 mg/mL) of 1000 ppm PHMB. The microgels were rehydrated in phosphate buffered saline at 300 mg/mL.

FIG. 10 shows a plot of modulus vs. frequency for the storage and loss moduli of 20:1 PEG-FGN gels without and with PHMB. The loss tangent for PEG-FGN was 0.25 while that of PEG-FGN-PHMB was 0.21 at an angular frequency of $1\ \text{sec}^{-1}$. The modulus data illustrates that the addition of PHMB increased the solid-like behavior of the PEG-FGN-PHMB complex in comparison to that of PEG-FGN, indicating that PHMB was incorporated covalently into the PEGylation reaction.

The covalent binding of PHMB into the PEGylated fibrinogen complex, forming a covalently bonded PEG-FGN-PHMB ternary complex, is supported in an antimicrobial study of the biocidal activity in a zone-of-inhibition (ZOI) study of PHMB that was included in the PEGylation of fibrinogen (covalently bound PHMB) and PHMB that was added subsequently to the formation of PEG-fibrinogen (unbound PHMB) against Methicillin resistant *Staphylococcus aureus* (MRSA, ATCC #700787). The ZOI for PEG-fibrinogen with unbound PHMB composite was <1.0 mm, while that of covalently bonded PHMB ternary composite had no measurable ZOI, with inhibition only under the microgel powder. Unbound cationic PHMB is expected to have a significantly larger ZOI because of the mobility of free PHMB, which may be ionically bound, not covalently bound, to anionic sites on fibrinogen, while the covalently bonded PHMB requires the microorganism to be in direct contact with the microgel particle.

In Vivo Subcutaneous Injection

PEG-FGN (20:1 molar) was evaluated alone and in combination with autologous stem cells (rat ADSCs) or BioDRestore™ morselized amnion. Microgels sterilized with ethylene oxide were injected into the rat dorsal subcutaneous region with a 21 gauge needle. Five test groups were evaluated in duplicate: rat ADSCs, BioDRestore™, PEG-FGN, PEG-FGN with rat ADSCs, and PEG-FGN with BioDRestore™. Results indicate that the microgels were easily injected, formed a cohesive solid, and remained at the injection site at days 7 and 14.

Hematoxylin & eosin (H&E) was used to stain the fixed tissue sections on days 7 and 14 to visualize the cells, collagen, and tissue remodeling. H&E staining showed minimal inflammatory response with host cell remodeling of the microgels. Remodeling of the microgels was even more evident on day 14, especially in combination with ADSCs or BioDRestore™.

Figure 11:
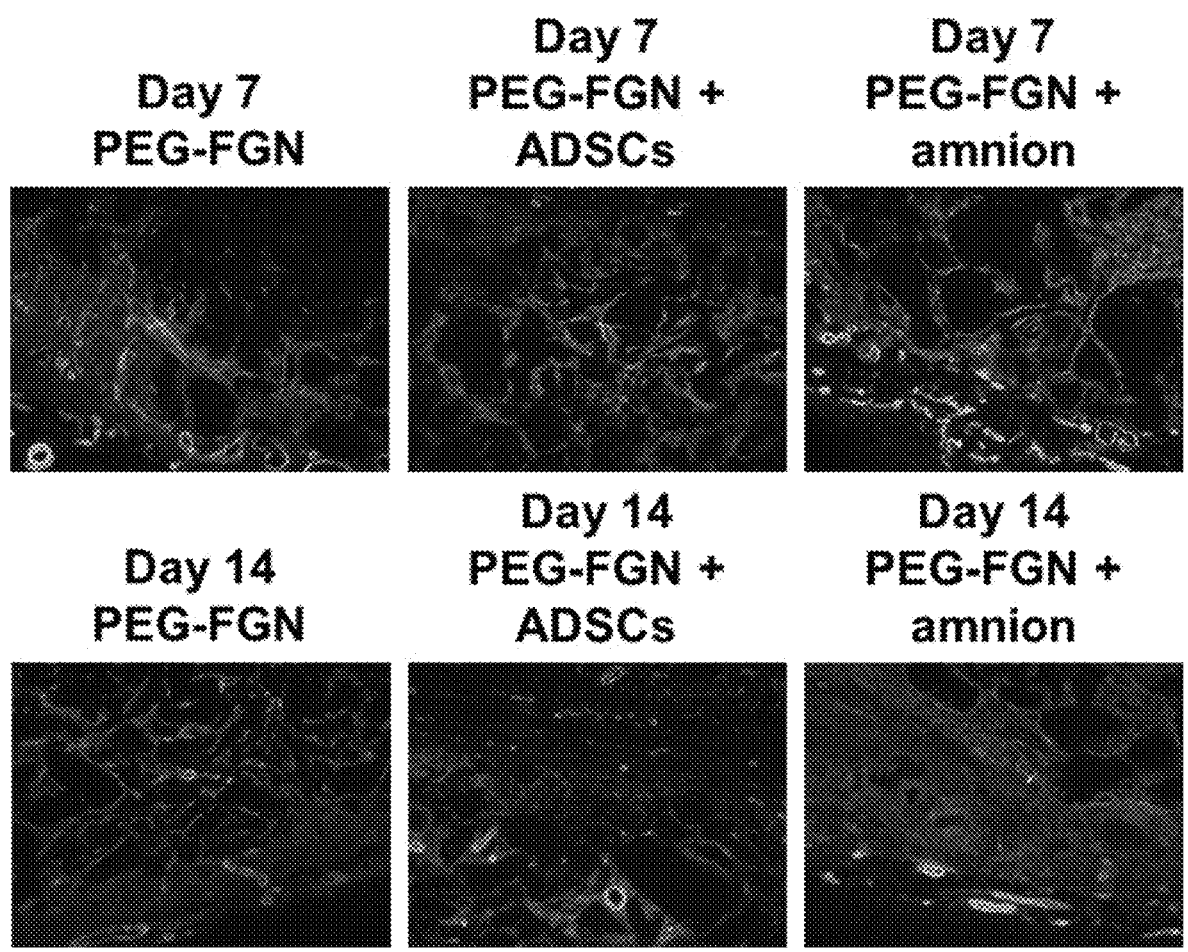
FIG. 11 shows images of smooth muscle actin (SMA) staining of 20:1 PEG-FGN microgels, which demonstrate angiogenesis at 7 and 14 days in the center of the microgels, alone and with incorporation of ADSCs or morselized amnion.

Smooth muscle actin (SMA) staining, an indicator for pericytes, showed blood vessel infiltration in microgels by days 7 and 14. Blood vessel formation was enhanced by the incorporation of allogeneic ADSCs or morselized amnion product (BioD) into the microgel system. FIG. 11 demonstrates blood vessel infiltration in the center of the microgels. With monolithic hydrogel systems, if angiogenesis occurs, it rarely reaches the center of the hydrogel.

Figure 12:
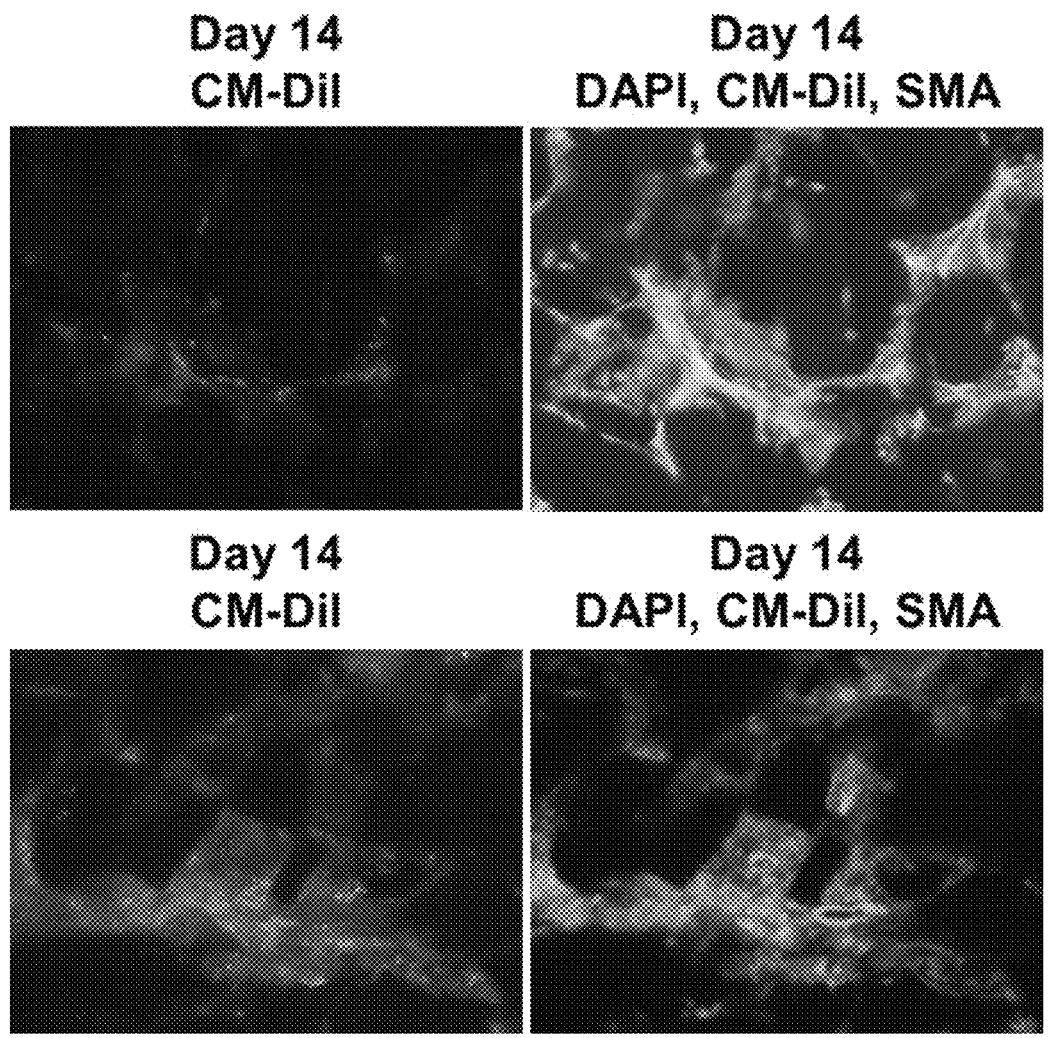
FIG. 12 shows images of CM-diI labeled rat ADSCs, indicating transplanted cell viability in 20:1 PEG-FGN microgels after 7 and 14 days. DAPI and smooth muscle actin (SMA) staining show cell nuclei and microvascular formation.

In addition, cell viability was enhanced by injection with the microgel particle system, which appears to shield the cells from shear stress. PEG-FGN microgel compositions injected with CM-diI labeled rat ADSCs ($2.0 \times 10^5$ cells/mL) were retained at the injection site at days 7 and 14. FIG. 12 demonstrates stem cell viability in the microgels after 7 and 14 days in vivo. DAPI nuclear staining and SMA staining for angiogenesis showed cells in the microgels were connected, spread out, viable, and promoted angiogenesis, even after 14 days in vivo.

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

The invention claimed is:

1. A composition comprising:
a plurality of water-insoluble, hydrogel microparticles comprising PEGylated gel microparticles comprising a protein or protein-based biological macromolecule crosslinked with a PEGylating agent;
where said protein or protein-based biological macromolecule is selected from the group consisting of collagen, gelatin, and combinations thereof;
wherein the PEGylating agent is α-succinimidyloxyglutaryl-ω-succinimidyloxyglutaryloxypolyoxyethylene (SG-PEG-SG);
wherein the plurality of water-insoluble, hydrogel microparticles are hydrated by an aqueous medium;
wherein the plurality of water-insoluble, hydrogel microparticles are obtained by lyophilizing and then grinding monolithic hydrogels;
wherein the composition includes clusters of the microparticles in the absence of shear, and the composition decreases in viscosity and exhibits viscoelastic solid properties with applied shear; and
wherein a molar ratio of PEGylating, agent to protein and/or protein-based biological macromolecule is from 10:1 to 50:1.

2. A composition comprising:
a plurality of water-insoluble, hydrogel microparticles comprising PEGylated gel microparticles comprising a protein or protein-based biological macromolecule crosslinked with a PEGylating agent that is difunctional to poly-functional;
where said protein or protein-based biological macromolecule is selected from the group consisting of gelatin, collagen, and combinations thereof;
wherein the plurality of water-insoluble, hydrogel microparticles are hydrated by an aqueous medium;
wherein the plurality of water-insoluble, hydrogel microparticles are obtained by lyophilizing and then grinding monolithic hydrogels;
wherein the composition includes clusters of the microparticles in the absence of shear, and the composition decreases in viscosity and exhibits viscoelastic solid and pseudoplastic properties with applied shear; and
wherein a molar ratio of PEGylating agent to protein and/or protein-based biological macromolecule is from 10:1 to 50:1.

3. The composition according to claim 2, wherein said composition has viscoelastic solid properties, a storage modulus greater than loss modulus, and a loss tangent value less than 1.

4. The composition according to claim 2, wherein storage modulus values of the composition, the plurality of water-insoluble; hydrogel microparticles, which are hydrated, or both, are between 10 Pa to 250,000 Pa and said loss modulus values are between 5 Pa to 100,000 Pa.

5. The composition according to claim 2, wherein the composition is in a form selected from the group consisting of solutions, suspensions, creams, lotions, gels, pastes, emulsions, balms, sprays, foams, aerosols, and other formulations thereof.

6. The composition of claim 2, wherein the pseudoplastic properties are independent of the aqueous medium used to hydrate the plurality of water-insoluble, hydrogel microparticles.

7. The composition of claim 2, wherein the plurality of water-insoluble, hydrogel microparticles are irregularly shaped and not spherical or elliptical.

8. The composition according to claim 2, wherein the plurality of water-insoluble, microparticles are in the form of a dry powder.

9. The composition according to claim 2, wherein said PEGylating agent is selected from α-succinimidyloxyglutaryl-ω-succinimidyloxyglutaryloxypolyoxyethylene (SG-PEG-SG), pentaerythritol tetra(succinimidyloxyglutaryl)polyoxyethylene, 4-aim succinimidyloxyglutaryl) polyoxyethylene, polyethylene glycol) di(proprionaldehyde), and combinations thereof.

10. The composition according to claim 2, further comprising an antibacterial agent, an antifungal agent, monoacyl glycerol, monoalkyl glycol, poly(hexamethylene biguanide) and its salts, and combinations thereof.

11. The composition according to claim 2, further comprising water-soluble polymers at a concentration of from 0.01 weight % to 25 weight %.

12. The composition according to claim 11, wherein the water-soluble polymers are selected from gelatin, albumin, pullulan, poly(L-lysine), and antimicrobial peptides.

13. The composition according to claim 2, further comprising a biological component.

14. The composition according to claim 13, wherein the biological component is selected from cells; micronized tissue and micronized decellularized tissue; synthetic or naturally derived extracellular matrix components; glycosaminoglycans, fibrin, laminin, fibronectin; hydroxyapatite; polysaccharides; poly(amino acids; and combinations thereof.

15. The composition according to claim 14, wherein the synthetic or naturally derived extracellular matrix components comprise collagen, glycosaminoglycans, fibrin, laminin or fibronectin.

16. The composition according to claim 2, further comprising at least one biologically active agent.

17. The composition according to claim 16, wherein the at least one biologically active agent is selected from antimicrobial agents, analgesic agents, anti-inflammatory agents, wound healing agents, Si-RNA, and combinations thereof.

* * * * *